US012741065B2

(12) United States Patent
Woo et al.

(10) Patent No.: US 12,741,065 B2
(45) **Date of Patent: *Sep. 22, 2026**

(54) WATER-BASED HYDROGEL BLEND COATING AND METHOD OF APPLICATION TO ELASTOMERIC ARTICLES

(71) Applicant: Allegiance Corporation, Waukegan, IL (US)

(72) Inventors: Choon Kong Woo, Bayan Lepas (MY); Chuang Sim Chong, Gelugor Pulau (MY); Nujalee Dangseeyun, Chonburi (TH); Panor Wannawong, Muang (TH)

(73) Assignee: ALLEGIANCE CORPORATION, Waukegan, IL (US)

(*) Notice: Subject to any disclaimer, the term of this patent is extended or adjusted under 35 U.S.C. 154(b) by 20 days.

This patent is subject to a terminal disclaimer.

(21) Appl. No.: 19/002,343

(22) Filed: Dec. 26, 2024

(65) Prior Publication Data

US 2025/0195728 A1 Jun. 19, 2025

Related U.S. Application Data

(60) Continuation of application No. 18/095,164, filed on Jan. 10, 2023, now Pat. No. 12,214,108, which is a (Continued)

(51) Int. Cl.
*C08J 7/04* (2020.01)
*A41D 19/00* (2006.01)
(Continued)

(52) U.S. Cl.
CPC .......... *A61L 31/10* (2013.01); *A41D 19/0082* (2013.01); *A61L 31/041* (2013.01);
(Continued)

(58) Field of Classification Search
CPC ............................ C09D 109/10; C09D 201/00
See application file for complete search history.

(56) References Cited

U.S. PATENT DOCUMENTS 3,714,100 A 1/1973 Biale et al.
3,813,695 A 6/1974 Podell et al.
(Continued)

FOREIGN PATENT DOCUMENTS

CA 2211561 A1 8/1996
CA 2211651 A1 8/1996
(Continued)

OTHER PUBLICATIONS

U.S. Appl. No. 18/095,164, filed Jan. 10, 2023.
(Continued)

*Primary Examiner* — Cachet I Proctor
(74) *Attorney, Agent, or Firm* — ArentFox Schiff LLP and Cardinal Health

(57) ABSTRACT

A water-based hydrogel polymer coating and a method of application to natural rubber or other elastomeric latex products are provided. The water-based hydrogel polymer is mixed with a blend of at least one elastomeric material to provide a hydrogel polymer blend composition. The water-based hydrogel polymer blend composition is applied in a single application to an elastomeric article, such as gloves, without additional solvents in the polymer blend composition and without a separate acid or chemical priming step. The water-based hydrogel coating herein provides increased lubricity to facilitate improved wet and dry donning of the elastomeric article.

16 Claims, 9 Drawing Sheets

Related U.S. Application Data continuation of application No. 16/834,579, filed on Mar. 30, 2020, now Pat. No. 11,577,009, which is a division of application No. 15/296,698, filed on Oct. 18, 2016, now Pat. No. 10,647,886.

(60) Provisional application No. 62/243,116, filed on Oct. 18, 2015.

(51) Int. Cl.

| | |
|---|---|
| ***A61L 31/00*** | (2006.01) |
| ***A61L 31/04*** | (2006.01) |
| ***A61L 31/10*** | (2006.01) |
| ***A61L 31/14*** | (2006.01) |
| ***B05D 1/02*** | (2006.01) |
| ***B05D 1/18*** | (2006.01) |
| ***B05D 3/00*** | (2006.01) |
| ***B05D 3/02*** | (2006.01) |
| ***B29C 33/42*** | (2006.01) |
| ***B29C 41/14*** | (2006.01) |
| ***B29D 99/00*** | (2010.01) |
| ***C08J 7/043*** | (2020.01) |
| ***C08J 7/056*** | (2020.01) |
| ***C09D 5/14*** | (2006.01) |
| ***C09D 7/47*** | (2018.01) |
| ***C09D 107/02*** | (2006.01) |
| ***C09D 109/04*** | (2006.01) |
| ***C09D 109/10*** | (2006.01) |
| ***C09D 201/00*** | (2006.01) |
| *A61B 42/10* | (2016.01) |
| *B29K 105/00* | (2006.01) |
| *B29L 31/48* | (2006.01) |

(52) U.S. Cl.

CPC ............. *A61L 31/14* (2013.01); *A61L 31/145* (2013.01); *B05D 1/02* (2013.01); *B05D 1/18* (2013.01); *B05D 3/007* (2013.01); *B05D 3/0254* (2013.01); *B29C 33/42* (2013.01); *B29C 41/14* (2013.01); *B29D 99/0067* (2013.01); *C08J 7/0427* (2020.01); *C08J 7/043* (2020.01); *C08J 7/056* (2020.01); *C09D 5/14* (2013.01); *C09D 7/47* (2018.01); *C09D 107/02* (2013.01); *C09D 109/04* (2013.01); *C09D 109/10* (2013.01); *C09D 201/00* (2013.01); *A61B 42/10* (2016.02); *A61L 2400/10* (2013.01); *A61L 2420/06* (2013.01); *B05D 2401/20* (2013.01); *B05D 2520/05* (2013.01); *B29K 2105/0064* (2013.01); *B29L 2031/4864* (2013.01); *C08J 2307/00* (2013.01); *C08J 2400/14* (2013.01); *C08J 2407/02* (2013.01); *C08J 2409/00* (2013.01); *C08J 2409/04* (2013.01)

(56) References Cited

U.S. PATENT DOCUMENTS 4,215,179 A 7/1980 Melamed et al.
4,233,362 A 11/1980 Novak et al.
4,252,852 A 2/1981 Goth
4,258,104 A 3/1981 Lee et al.
4,482,577 A 11/1984 Goldstein et al.
4,499,154 A * 2/1985 James .................... B29C 41/14 428/521
4,510,204 A 4/1985 Duke et al.
4,546,014 A 10/1985 Gajria et al.
4,562,226 A 12/1985 Coombes et al.
4,575,476 A 3/1986 Podell et al.
4,837,057 A 6/1989 Bartoszek-Loza et al.
4,975,484 A 12/1990 Fryd et al.
4,980,410 A 12/1990 Fryd et al.
4,990,357 A 2/1991 Karakelle et al.
5,084,514 A 1/1992 Szczechura et al.
5,085,140 A 2/1992 Kunig
5,314,741 A 5/1994 Roberts et al.
5,483,697 A 1/1996 Fuchs
5,486,426 A 1/1996 Mcgee et al.
5,492,500 A 2/1996 Sinclair et al.
5,516,865 A 5/1996 Urquiola
5,545,451 A 8/1996 Haung et al.
5,576,072 A 11/1996 Hostettler et al.
5,649,326 A 7/1997 Richard et al.
5,688,855 A 11/1997 Stoy et al.
5,723,273 A 3/1998 Anderson et al.
5,723,274 A 3/1998 Anderson et al.
5,742,943 A 4/1998 Chen
5,786,135 A 7/1998 Anderson et al.
6,077,602 A 6/2000 Liestman et al.
6,248,826 B1 6/2001 Solomon et al.
6,280,673 B1 8/2001 Green et al.
6,306,514 B1 10/2001 Weikel et al.
6,347,408 B1 2/2002 Yeh
6,353,148 B1 * 3/2002 Gross ..................... A61L 15/42 526/240
6,376,600 B1 4/2002 Solomon et al.
6,391,409 B1 * 5/2002 Yeh ...................... B29C 41/003 428/521
6,465,591 B1 10/2002 Lee
6,476,119 B1 11/2002 Kucera et al.
6,624,274 B1 9/2003 Suddaby
6,652,937 B1 11/2003 Guo et al.
6,706,313 B1 3/2004 Goldstein et al.
6,709,725 B1 3/2004 Lai et al.
6,767,310 B2 7/2004 Amanuma et al.
6,772,443 B2 8/2004 Soerens et al.
6,895,600 B2 5/2005 Williams
7,032,251 B2 4/2006 Janssen
7,179,415 B2 2/2007 Teoh et al.
7,329,442 B2 2/2008 Modha et al.
7,341,962 B2 3/2008 Kitamura
7,455,863 B2 11/2008 Hamann
7,566,502 B1 7/2009 Chen et al.
7,585,526 B2 9/2009 Hamann
7,767,251 B2 8/2010 Wang et al.
7,771,644 B2 8/2010 Flather et al.
7,794,839 B2 9/2010 Schmidt et al.
7,971,276 B2 7/2011 Eng et al.
7,988,983 B2 8/2011 Yu et al.
8,076,445 B2 12/2011 Shane et al.
8,110,266 B2 2/2012 Chen et al.
8,137,735 B2 3/2012 Wang et al.
8,187,684 B2 5/2012 Teoh et al.
8,250,672 B2 8/2012 Lipinski et al.
8,399,105 B2 3/2013 Butz et al.
8,499,363 B2 8/2013 Chou et al.
8,656,518 B2 2/2014 Saunders et al.
8,835,014 B2 9/2014 Wang et al.
8,980,391 B2 3/2015 Chen et al.
9,085,663 B2 7/2015 Chen et al.
9,149,567 B2 10/2015 Eng et al.
9,821,092 B2 11/2017 Bengtson
11,357,715 B2 6/2022 Lev
2005/0127552 A1 * 6/2005 Modha ................... A61L 31/10 264/129
2005/0132466 A1 6/2005 Janssen et al.
2005/0171248 A1 8/2005 Li et al.
2006/0141186 A1 6/2006 Janssen et al.
2006/0218697 A1 10/2006 Modha et al.
2007/0048445 A1 3/2007 DiMario
2007/0104904 A1 * 5/2007 Hamann ................ B32B 25/00 428/35.7
2007/0120294 A1 5/2007 Peng et al.
2007/0136926 A1 6/2007 Johnson et al.
2007/0160754 A1 7/2007 Blaise-Graftieaux et al.
2007/0243372 A1 10/2007 Mowrey et al.
2008/0124560 A1 5/2008 Marcu et al.
2009/0035447 A1 2/2009 Bottcher
2009/0068443 A1 3/2009 Curtet et al.

(56) References Cited

U.S. PATENT DOCUMENTS

| | | | |
|---|---|---|---|
| 2009/0292081 | A1 | 11/2009 | Suddaby |
| 2010/0050311 | A1 | 3/2010 | Tsai |
| 2010/0068399 | A1 | 3/2010 | Chernyshov et al. |
| 2010/0255329 | A1 | 10/2010 | Couvreur |
| 2010/0263106 | A1 | 10/2010 | Kassam et al. |
| 2010/0316588 | A1 | 12/2010 | Messier et al. |
| 2011/0077355 | A1 | 3/2011 | Shikisai et al. |
| 2011/0099688 | A1 | 5/2011 | Saleh |
| 2011/0145975 | A1 | 6/2011 | Eng et al. |
| 2011/0191936 | A1 | 8/2011 | Lipinski et al. |
| 2012/0065323 | A1 | 3/2012 | Overton et al. |
| 2012/0246799 | A1 | 10/2012 | Khoo et al. |
| 2013/0095257 | A1 | 4/2013 | Mizusaki et al. |
| 2014/0000006 | A1 | 1/2014 | Perera et al. |
| 2014/0171328 | A1 | 6/2014 | Armstrong et al. |
| 2014/0342096 | A1 | 11/2014 | Hsu et al. |
| 2015/0128329 | A1 | 5/2015 | Amarasekera et al. |
| 2015/0135403 | A1 | 5/2015 | Mercado et al. |
| 2015/0143608 | A1 | 5/2015 | Loo et al. |
| 2015/0157072 | A1 | 6/2015 | Megat et al. |
| 2017/0107403 | A1 | 4/2017 | Woo et al. |
| 2017/0130018 | A1 | 5/2017 | Chen et al. |

FOREIGN PATENT DOCUMENTS

| | | | | |
|---|---|---|---|---|
| CA | 2413094 | A1 | | 12/2001 |
| CA | 2448475 | A1 | | 5/2004 |
| CA | 2448475 | C | * | 1/2009 |
| CN | 101674897 | A | | 3/2010 |
| EP | 0396431 | A1 | | 11/1990 |
| EP | 1838767 | A1 | | 10/2007 |
| JP | H10-502856 | A | | 3/1998 |
| JP | 2007-518829 | A | | 7/2007 |
| JP | 2023-078125 | A | | 6/2023 |
| WO | 96/23602 | A1 | | 8/1996 |
| WO | 2006/071308 | A1 | | 7/2006 |
| WO | 2014/203075 | A2 | | 12/2014 |
| WO | 2015/006806 | A1 | | 1/2015 |
| WO | 2017/070100 | A1 | | 4/2017 |
| WO | 2017/164902 | A1 | | 9/2017 |

OTHER PUBLICATIONS

U.S. Appl. No. 16/834,579, filed Mar. 30, 2020.

U.S. Appl. No. 15/296,698, filed Oct. 18, 2016.

Agrawal et al., 'Strong Fiber-Reinforced Hydrogel', Acta Biomaterialia, vol. 9, Oct. 27, 2012, pp. 5313-5318.

Hydrogels—Wikipedia, the free Encyclopedia, retrieved on Aug. 14, 2015, 1 page.

Sankar et al., "Application of Poly Ethylene Glycol Hydrogel to Overcome Latex Urinary Catheter Related Problems", BioFactors, vol. 30, No. 4, Dec. 19, 2008, pp. 217-225.

* cited by examiner

WATER-BASED HYDROGEL BLEND COATING AND METHOD OF APPLICATION TO ELASTOMERIC ARTICLES

CROSS-REFERENCE TO RELATED APPLICATIONS

This application is a continuation of U.S. patent application Ser. No. 18/095,164, WATER-BASED HYDROGEL BLEND COATING AND METHOD OF APPLICATION TO ELASTOMERIC ARTICLES, filed Jan. 10, 2023, which is a continuation of U.S. patent application Ser. No. 16/834,579, titled WATER-BASED HYDROGEL BLEND COATING AND METHOD OF APPLICATION TO ELASTOMERIC ARTICLES, filed on Mar. 30, 2020, now U.S. Pat. No. 11,577,009, which is a divisional of U.S. patent application Ser. No. 15/296,698, titled "WATER-BASED HYDROGEL BLEND COATING AND METHOD OF APPLICATION TO ELASTOMERIC ARTICLES", filed on Oct. 18, 2016, now U.S. Pat. No. 10,647,886, which claims priority to U.S. Provisional Application No. 62/243,116, titled "WATER-BASED HYDROGEL BLEND COATING AND METHOD OF APPLICATION TO ELASTOMERIC ARTICLES", filed on Oct. 18, 2015, the disclosure of each application hereby incorporated by reference in its entirety.

FIELD

A water-based hydrogel coating for natural rubber or synthetic rubber articles is provided herein and methods of applying said coatings and, in particular, a water-based hydrogel coating blend that comprises a blend of hydrogel and elastomeric materials.

BACKGROUND

Medical articles, such as gloves and other elastomeric articles, often come into contact with liquids and fluids during their use. Such articles form a barrier between the user's skin and the external environment. Medical gloves, such as examination gloves and surgical gloves are examples of articles used in the healthcare setting, and they play a key role in minimizing the spread of infectious diseases. Such articles are used frequently by health care professionals. Therefore, it is important for medical articles such as gloves to provide an effective barrier, while providing an adequate level of comfort to the user. On the other hand, an uncoated latex article, such as a surgical glove, can have poor lubricity making it difficult for the user to don the glove, e.g., place the glove on a human hand, in both wet donning (e.g., donning the glove when the skin is damp) and dry donning (e.g., donning the glove when the skin is dry). Thus, the application of a coating to these elastomeric articles can be used to provide a smooth and non-tacky inner skin-contacting surface, e.g., to facilitate donning the article to which the coating has been applied. These coated articles also preferably have a coating that does not flake off.

It is known in the art to utilize lubricants or other coatings on rubber and synthetic latex products, such as surgical gloves, condoms, finger cots, catheters, probe covers, ureters, and the like, for enhancing the lubricity of the product when it comes into contact with the skin of the user. One such approach was to utilize lubricants that included powders, such as calcium carbonate and corn starch, applied to the inner skin-contacting surface of a surgical glove to ease donning of the glove. However, powdered lubricants can be unfavorable due to the risk of the powdered lubricant leaking out of the interior of the glove and contaminating the surgical field. Moreover, certain starch powders can be carriers of latex allergens that can cause latex allergies in some users of the gloves.

In other approaches, a lubricant coating is applied to the interior surface of the glove that does not contain a powder. In one instance, a polymeric coating, such as a hydrogel coating, can be applied to the glove. Where a hydrogel coating is applied to the glove, it is often provided in a solvent medium, such as ethanol, to maintain the polymers in solution. The use of a solvent system in a polymer solution is undesirable because the solvent is typically expensive, can create a fire hazard and provides a waste disposal issue making it not environmentally friendly. Moreover, the solvent-based hydrogel polymer solutions tend to have a short pot-life, e.g., of only a few weeks, in which the solution must be used and applied as a coating.

In addition to the formulation of these hydrogel coatings containing unfavorable solvent-based systems, the method of application of these solvent-based systems can provide expensive and onerous steps. In particular, prior to application of the polymeric coating to the surface of the glove, for example, the latex or rubber is heat dried and then further treated with a chemical priming step to prepare the rubber or latex surface for receiving the hydrogel polymer solvent-based coating. The chemical priming step can include dipping the rubber or latex article in an acid solution or other harsh chemical prior to the subsequent dip in the coating solution. Following dipping in acid or other harsh chemical, the article is rinsed to remove any residual acid or chemical. The use of a chemical priming step in a glove coating process provides an additional, undesirable step that is time consuming and expensive. Moreover, the acid or chemical used during the priming step must also be later disposed of, creating an additional waste disposal step and providing an added cost.

After application of the solvent-based hydrogel coating, an additional process step is needed to dispose of the solvent waste. Since the solvent is not environmentally friendly it requires special treatment prior to disposal. Moreover, extra precautions and steps need to be taken to make the process fire-proof to prevent any ignition from the flammable solvents being used with the hydrogel solution.

A need, therefore, exists for a water-based hydrogel coating for elastomeric articles.

SUMMARY

A water-based hydrogel coating is provided that facilitates improved lubricity of an elastomeric article coated with the water-based hydrogel coating and, in the case of a glove, improved donning. In particular, a water-based hydrogel blend coating solution is provided that comprises a water-based hydrogel and at least one elastomeric material without requiring a solvent medium. In addition, a method of applying the water-based hydrogel blend coating composition to elastomeric articles is provided having an improved process that does not require an acid priming or other chemical priming step. In one embodiment, the hydrogel blend coating composition can be provided such that at least one of the elastomeric components of the hydrogel blend solution is the same as or similar to the elastomeric material of the final elastomeric article.

A water-based hydrogel coating can be formed by combining a water-based hydrogel with one or more elastomeric materials and, in one aspect, with a blend of two or more elastomeric materials to form a water-based hydrogel blend coating. In one aspect, the elastomeric blend can comprise two or more elastomeric materials and, in one instance can comprise nitrile rubber and another elastomer similar to the base article material. This water-based hydrogel blend can be applied to either natural or synthetic rubber latex materials to result in a final article that is coated on at least one surface with the hydrogel blend coating. The final article that is coated can be any elastomeric article that can benefit from an improved lubricity and, in one aspect, can include, but is not limited to, medical gloves, surgical gloves, examination gloves, industrial gloves, condoms, finger cots, probe covers, catheters, ureters, and the like.

The blended formulation allows for a coating solution having a higher solids content, which is beneficial in improving the lubricity of the final elastomeric article, and that remains adhered to the article despite having high solids content. In contrast, a non-blended formulation cannot retain coating adherence at similarly high solids content, thus, being unable to coat at a high solids content onto an elastomeric article. Higher solids content allows for more coating to be applied per surface area of the glove, which in turn provides an increased lubricity. The final coated elastomeric article, coated with the water-based hydrogel blend disclosed herein, can have an improved lubricity than an article coated with the hydrogel alone and can further facilitate both improved donning of an elastomeric glove article, for example, when the skin is damp (e.g., wet donning) and donning when the skin is dry (e.g., dry donning).

A method of applying the water-based hydrogel blend coating to an elastomeric article can reduce the number of process steps required as compared to previous solvent-based coating processes. In particular, an acid or other chemical priming step prior to application of the hydrogel blend coating is not required. In one aspect, an elastomeric glove material can be coated in a process with the hydrogel blend coating disclosed herein. The glove material can be made by conventional glove forming processes, such as coagulant dipping. After a glove former is dipped into the latex material, it can be dried and dipped again into the hydrogel blend coating, without requiring an acid priming step or other chemical priming step. In another aspect, gloves can be provided with the coating material for improved wet and dry donning of the glove and further provided with a textured surface for improved grippability of the glove while in use.

The water-based hydrogel blend is advantageous because it is solvent-free, which can avoid some of the flammability issues associated with using a solvent-based hydrogel in a manufacturing facility. In addition, there is less material waste and disposal due to the water-based formulation compared to the solvent-based formulation, making the water-based formulation more environmentally friendly. The solvent-based formulation requires disposal of the hazardous solvent material which adds cost, processing time and is not friendly to the environment. Moreover, the shelf-life of the water-based hydrogel blend is increased compared to the solvent-based hydrogel system such that the water-based hydrogel blend formulation can be stored for a longer period of time prior to use.

It is further advantageous to coat an elastomeric article with the water-based hydrogel blend in comparison to coating with only the hydrogel coating alone. The hydrogel blend mixture has improved mechanical and thermal stability compared to the hydrogel coating mixture alone. In addition, the hydrogel blend has superior adhesion to the elastomeric substrate compared to the hydrogel coating alone. Application of the hydrogel only to the elastomeric article as the coating can pose some technical challenges. One of the challenges is that a hydrogel only coating on an elastomeric article can delaminate from the elastomeric article substrate. To overcome the issue of delamination, the surface of the elastomeric article can be primed with harsh chemicals; however, this can cause the deterioration of physical properties of the elastomeric article itself. Another approach to overcome delamination can be to coat the elastomeric article with a low total solid of the coating solution; however, a low total solid can reduce the coating performance which in turn can result in a poor dry or wet lubricity. Another approach can be to modify the hydrogel only material by inclusion of polymer lattices.

In one aspect, an elastomeric glove can be formed and then coated with the water-based hydrogel blend disclosed herein. The glove, in one embodiment, can be formed from natural rubber latex and then dipped into the hydrogel blend comprising the hydrogel, natural rubber and a second elastomeric article, such as nitrile latex. The amount of natural rubber in the blend can be greater than the amount of nitrile latex in the blend. In another aspect, the amount of natural rubber latex can be the same as the nitrile latex in the blend. In yet another aspect, the amount of nitrile in the blend can be greater than the natural rubber.

In another embodiment, the glove can be formed from a synthetic rubber latex and then coated in a hydrogel blend comprising the hydrogel, synthetic rubber and a second elastomeric article. The glove, in one embodiment, can be formed from synthetic rubber latex and then dipped into the hydrogel blend comprising the hydrogel, synthetic rubber and a second elastomeric article, such as nitrile latex. The amount of synthetic rubber in the blend can be greater than the amount of nitrile latex in the blend. In another aspect, the amount of synthetic rubber latex can be the same as the nitrile latex in the blend. In yet another aspect, the amount of nitrile in the blend can be greater than the synthetic rubber. In a preferred embodiment, the synthetic rubber of the article and the blend is polyisoprene. In yet another embodiment, at least one of the elastomeric materials present in the hydrogel blend can be the same as the elastomeric material used in the elastomeric article.

DETAILED DESCRIPTION

Figure 1:
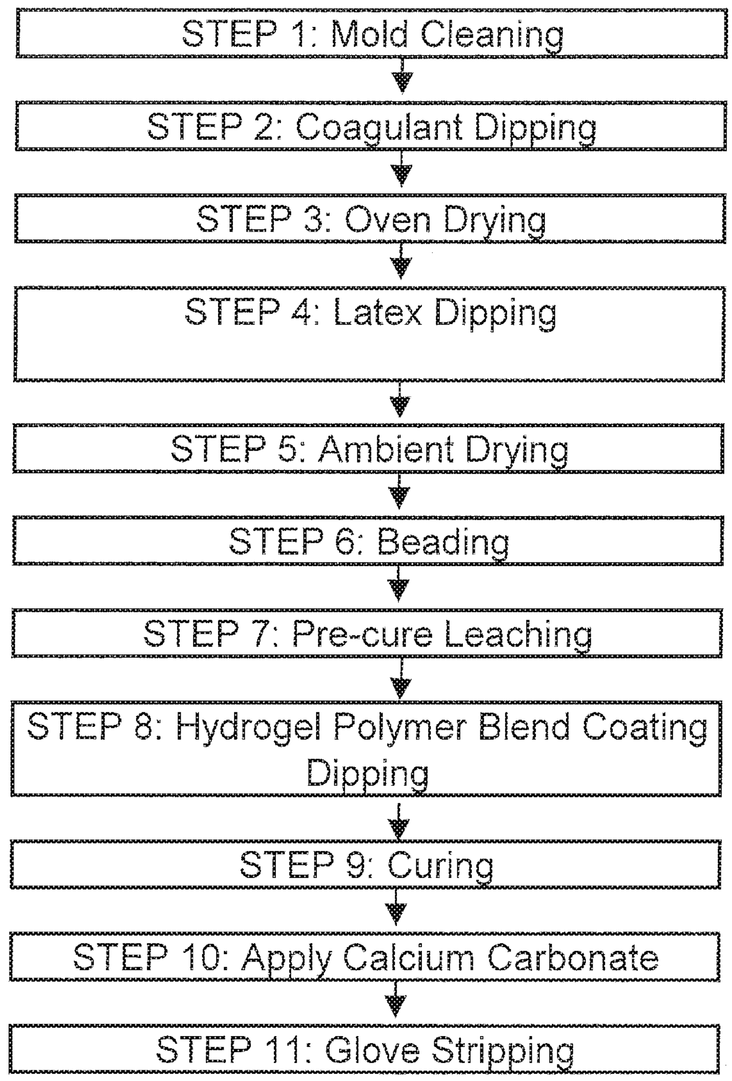
FIG. 1 is a flow diagram of an exemplary coating process using the water-based hydrogel blend disclosed herein.

An aqueous polymer blend composition for application as a coating to elastomeric articles and a method of applying the coating to the elastomeric articles are described herein and provided in FIGS. 1-8B. The polymer blend composition can be formed by blending together at least one elastomeric material and a water-based hydrogel composition and, in one aspect, at least two elastomeric materials with the water-based hydrogel. In another aspect, the blend of elastomeric materials can comprise a blend of natural rubber and nitrile especially where the elastomeric article to be coated is made from natural rubber. In yet another aspect, the blend of elastomeric materials can comprise a blend of synthetic rubber and nitrile, especially where the elastomeric article to be coated is made from synthetic rubber. In one embodiment, the synthetic rubber is polyisoprene. The coating material can improve lubricity of the elastomeric article and, in the instance of elastomeric gloves, improve donning ability of the glove by the user. In particular, the application of the coating to at least one surface of the glove (e.g., an inner skin-contacting surface) can eliminate the need to add a powder material or other lubricant to the skin-contacting surface of the glove for donning purposes. Thus, the coated glove can be powder-free.

The polymer blend composition includes a water-based hydrogel polymer. The hydrogel polymer can be a hydrophilic polymer. The hydrogel can also be an acrylic polymer. In one embodiment, it can be a synthetic acrylic polymer. The hydrogel polymer can comprise any that are known in the art and, in one aspect, can be a water-based hydrogel polymer as provided by Nobel Synthetic Polymer Sdn. Bhd., from Selangor, Malaysia. In one aspect, the hydrogel polymer can comprise greater than about 15% synthetic acrylic polymer, less than about 5% additives and the remaining amount made up of water. The acrylic polymer can be any known in the art. The amount of hydrogel provided in the final hydrogel blend composition can comprise a majority of the hydrogel in comparison to the at least one or more elastomeric materials.

The elastomeric materials provided in the polymer blend composition can be any that are typically used in the production of elastomeric articles, and can include natural rubber and/or synthetic elastomers. Natural rubber that can be used includes rubber made from hevea rubber latex and guayule rubber latex, and any other natural rubbers known in the art. Synthetic rubber elastomers which can be used, include polyisoprene, polychloroprene, polyurethane, polybutadiene, nitrile, styrene butadiene rubber, block copolymers of styrene and butadiene, block copolymers of styrene and isoprene, mixtures of these elastomers and vinyl, and the like. Other synthetic rubbers that can be used include acrylic diene block copolymers, acrylic rubber, butyl rubber, EPDM rubber, chlorosulfonated polyethylene rubber and fluororubber. In one aspect, at least one of the elastomeric materials can be chosen such that it is the same material or similar to the base material of the elastomeric article. For example, if the elastomeric article is a glove made from natural rubber then the hydrogel blend can comprise at least the hydrogel and natural rubber in the coating composition. In another instance, if a glove material is made from synthetic polyisoprene latex material, then the hydrogel blend composition can include hydrogel and at least synthetic polyisoprene as the elastomeric component, and so on. In another instance, the elastomeric material can be different from the elastomeric article. For instance, a natural rubber elastomeric article, the hydrogel blend can include hydrogel and at least one synthetic rubber elastomer.

In one embodiment, the hydrogel blend composition can comprise the hydrogel mixed with a first elastomeric material that corresponds to the same material as the base material of the final article, and optionally a second elastomeric material that is different from the first. Thus, in one aspect, where the elastomeric article is made from natural rubber, the hydrogel blend component can comprise a first elastomeric material that is natural rubber and a second elastomeric material that is nitrile, for example, or another elastomeric polymer different from the first. In another embodiment, where the elastomeric article is a natural rubber glove, the hydrogel blend composition can contain natural rubber latex as one of the elastomeric materials and, in one example, can contain natural rubber latex in an amount of up to about 37 phr. In another aspect, the natural rubber latex can be included in the blend at an amount of about 12.5 to about 37 phr, and in particular, can be 19 phr. The second elastomeric material in the hydrogel blend can comprise, for example, a nitrile latex. The nitrile latex can be included in an amount of up to about 25 phr. In another instance, the nitrile latex can be included in the blend at an amount of about 0.5 to 25 phr, and, in particular, in an amount of about 6 phr. Where the nitrile latex can have bound acrylonitrile content of about 28%.

In another embodiment, where the elastomeric article is a glove made from synthetic rubber, specifically such as from polyisoprene, the hydrogel blend can comprise an elastomeric material that is similar to the base glove material, i.e., polyisoprene. The polyisoprene or other synthetic rubber in the blend can be included at levels up to about 15 phr and, in particular, in amounts of about 7.5 phr. In one aspect, the polyisoprene can be in the amount of about 4 to 11 phr. In addition, the polyisoprene blend can also include a second elastomeric material in the coating solution and, in one example; the second elastomer can be nitrile. The nitrile latex can be included in an amount up to about 15 phr and, in particular, in an amount of about 7.5 phr. In one aspect, the nitrile can be include in the amount of about 4 to about 11 phr. The nitrile latex can have bound acrylonitrile content of about 28%.

Without being bound by theory, it is believed that by introducing at least one additional elastomeric material to the blend already comprising the first elastomeric material corresponding to the base material, that this additional elastomeric component can disrupt the continuous film property of the water-based hydrogel coating, and can further provide interstices and an irregular domains for upholding lubricant loading and reducing contact surface with the skin of the user, hence dry and damp donning of the final coated article can be achieved, increasing lubricity. In effect, the first elastomeric material similar to the base material of the article can provide adhesion of the hydrogel coating to the article while the addition of the at least second elastomeric material, different from the first, can disrupt the continuous flow of the coating and thus result in a unique morphology on the surface that is not flat but provides some peaks and valleys which can improve donnability. The hydrogel blend coating can also reduce the stickiness when the glove is pressed flat for packaging, such that the two inner coated surfaces of the same glove come into contact and do not stick together as much as a glove coated with the hydrogel only coating. Where only one elastomeric material is provided with the hydrogel, the coating surface can become rather flat. In contrast, where at least a second elastomeric material is added to the blend this provides for a surface having more interstices and the irregular domains which can result in a textured surface being produced on the coated surface of the glove. The textured surface can reduce the contact surface with skin of the user since only protruding "peaks" of the coating contact the skin of the user, thus improving donning. By including at least one elastomeric material that is similar to the base material of the elastomeric article it is believed that the combination can also provide a chemical affinity necessary to enhance adhesion of the water-based hydrogel blend to the base elastomer article. This can further be beneficial to allow treatment with a higher level of lubricant (such as cetylpyridinium chloride (CPC)). If the coating adhesion is not good, i.e., as in the case of a hydrogel-only coating, the coating will detach from the elastomer surface in particular when treated with a high level of lubricant (e.g., CPC). A higher level of CPC added to the coated glove can also help with improved wet donning of the glove.

In one aspect, where the final elastomeric article to be coated is a glove, such that, for example, the base glove is made from natural rubber, the natural rubber used to make the base glove may be compounded with stabilizers, a crosslinker, a vulcanization activator, a vulcanization accelerator, an antioxidant, an antiozonant and optionally, white or other colored pigments. In another aspect, where the final elastomeric article to be coated is a glove, such that, for example, the base glove is made from synthetic rubber, such as polyisoprene, the polyisoprene used to make the base glove may be compounded with stabilizers, a crosslinker, a vulcanization activator, a vulcanization accelerator, an antioxidant, an antiozonant and optionally, white or other colored pigments.

The water-based hydrogel blend composition can comprise about 50% to about 99% hydrogel, from about 0.5% to about 37% of a first elastomer, and about 0.5% to about 25% of a second elastomer. In one example, the final coating composition can comprise about 75% of the water-based hydrogel in the coating composition with the elastomer blend comprising about 25%. In another embodiment, the hydrogel blend composition can comprise from about 50% to about 99% hydrogel, from about 0.5% to about 37% of natural rubber latex, and about 0.5% to about 25% of nitrile latex. In one embodiment, the hydrogel blend can comprise 75-85% hydrogel, 19% natural rubber, and 6% nitrile. In yet another embodiment, the hydrogel blend can comprise about 12% to about 40% of a first elastomer material with the second elastomer material making up the rest of the coating composition after the hydrogel is incorporated and, in one instance, the first elastomer material can comprise about 12.5% to about 37%. Where only one elastomeric material is blended with the hydrogel, the hydrogel can be provided at a range of about 50% to about 99% hydrogel by weight of the coating solution and the one elastomeric material can be provided from about 5% to about 35%. In another embodiment having a synthetic rubber latex article, such as polyisoprene, the hydrogel blend composition can comprise from about 75% to about 85% of the water-based hydrogel with the elastomer blend comprising about 10% to about 20% of the hydrogel blend composition. In one example, the hydrogel blend is from 75-85% hydrogel and can comprise from about 4% to about 11% of a first elastomer material, such as a polyisoprene latex, and a second elastomer material from about 4% to about 11%, such as of nitrile latex. In another example, the hydrogel blend is from 75-85% hydrogel and can comprise about 7.5% of a first elastomer material, such as polyisoprene, and 7.5% of a second elastomer material, such as nitrile.

The hydrogel blend composition can have a higher total solids content in comparison to the hydrogel alone and, in particular, the hydrogel blend composition can have a total solids content between about 3.0% to about 7%. In one instance, a range of total solids content from 3.5% to about 5% can be provided. In one aspect, a total solids content of about 4% is targeted.

Coating the elastomeric article with only the hydrogel composition alone, having no elastomeric materials added, and results in poor coating adhesion to the elastomeric article. In particular, a hydrogel-only coating can result in a coating that flakes off of the coated elastomeric article and the coating can also become abraded during the chlorination process. Moreover, when the elastomeric article formed is a glove an internal tackiness is noticed. In addition, the total solids content of an all-hydrogel coating, if too high or too low, can lead to poor results such as internal tackiness, poor donning properties, and a "wet" look of the final article. Finally, if a post treatment with a lubricant, such as CPC, is performed to an article coated with a hydrogel-only coating composition, the amount of the lubricant must be reduced significantly so that the powder content can meet the specification for powder-free gloves, otherwise the hydrogel-only coating can detach from the surface of the elastomeric article and form powder particulate.

In contrast, the hydrogel blend coating composition has improved adhesion to the elastomeric article in comparison to the hydrogel-only coating. Moreover, a high solids content of the blend coating can be used without any issues observed in the final article, which is desirable since higher solids content improves the final lubricity of the article. The hydrogel blend coating also can provide a unique coating surface morphology of the coated article which can prevent internal tackiness, facilitates improved donning of the article, such as a glove, and prevents the appearance of a "wet" look of the final article. In addition, the hydrogel blend coating composition can enable a more robust post treatment process, such as treating the coated gloves with a higher amount of lubricant.

The water-based polymer blend composition can have a shelf-life that is much longer than a solvent-based polymer composition. A solvent-based polymer composition used in coating gloves typically has a very short pot-life, which can impose constraints on the process, e.g., requiring almost immediate use of the solvent-based materials once made. In contrast, the water-based polymer blend can be stored for longer periods of time, which allows for longer storage of the composition prior to use. For instance, the pot-life for a solvent-based polymer composition may be from about 3 to about 4 weeks, whereas the pot-life for a water-based polymer blend composition as disclosed herein can be up to about 6 months.

In addition, the water-based polymer blend is safer to manufacture and use in the manufacturing facility because it is free from fire hazards as compared to the solvent-based material. The main component of the solvent-based polymer coatings is a solvent based material, e.g., alcohol, which is easily ignitable. In implementing the water-based polymer blend, no additional capital investments are needed to address safety concerns during operation, which makes the water-based polymer blend coating easier to implement across different manufacturing platforms. Where the solvent-based material can have high disposal costs due to special treatment of the solvent as well as not being environmentally friendly, the water-based polymer blend is much easier and much less costly to handle through existing waste water treatment set-ups in the facilities.

The elastomeric articles that can be coated with the aqueous polymer blend disclosed herein can be any elastomeric articles that may benefit from an improved lubricity to the final product. Examples of elastomeric materials that can be used to make the articles can include, but are not limited to, natural rubber and synthetic rubber latex materials, such as polyisoprene, polychloroprene, polyurethane, polybutadiene, nitrile, block copolymers of styrene and butadiene, block copolymers of styrene and isoprene, and the like. Examples of the final article that results from the elastomeric materials chosen can include gloves, catheters, condoms, probe covers, finger cots, ureters, and the like.

In one aspect, the elastomeric material can be formulated into a glove and, in particular a surgeon's glove or an exam glove. After the glove is formed, it can be dipped into the polymer blend composition to coat at least one surface of the glove. It is preferred to coat at least the inner surface, i.e., skin-contacting surface, of the glove. When the glove is formed on a former or glove mold or mandrel, for example, it is the skin-contacting surface that is exposed or positioned externally on the glove former. Thus, when the glove is dipped into the aqueous solution of the polymer blend, although the exterior surface is being coated, that surface will later become the skin-contacting internal surface after the glove is removed and reversed from the mold.

In another aspect, the elastomeric material can comprise a natural rubber material formulated into a glove by dipping a glove former into the natural rubber latex material and then dipping the natural rubber glove into the polymer blend composition to coat at least one surface of the glove. In yet another aspect, the elastomeric material used for the final product can comprise a synthetic polyisoprene material that is first formed into a glove by dipping the glove former into the polyisoprene latex material and then dipping into the polymer blend coating solution. A similar process can be implemented for any elastomeric material chosen.

In one embodiment, the polymer blend composition can comprise about 75 wt % of the water-based hydrogel, about 19 wt % natural rubber latex and about 6 wt % nitrile latex. In another embodiment, the polymer blend composition can comprise about 75 wt % water-based hydrogel by weight and about equal amounts of the elastomeric materials or about 12.5 wt % of each. In yet another embodiment, the polymer blend composition can comprise about 75 wt % water-based hydrogel, about 6 wt % natural rubber latex and about 19 wt % nitrile latex. In one instance, a polymer blend composition can comprise about 85% hydrogel, 4% polyisoprene, and 11% nitrile. In another instance, a polymer blend composition can comprise about 85% hydrogel, 11% polyisoprene, and 4% nitrile. In another instance, a polymer blend composition can comprise about 85 wt % hydrogel and about 7.5 wt % polyisoprene with about 7.5 wt % nitrile.

Optionally, other ingredients such as surfactants or biocides may be added to the coating composition. Possible surfactants may be anionic and/or nonionic surfactants, for example, sodium lauryl sulfates and/or ethoxylated nonylphenols. The anionic and/or non-ionic surfactants can help to enhance coating stability in particular when elastomeric materials are added to the coating composition. In one aspect, a non-ionic surfactant such as Igepal CO 630 can be provided or other similar surfactants. In another aspect, an anionic surfactant such as Darvan® WAQ can be provided or other similar surfactants. In one embodiment, a non-ionic and an anionic surfactant are added. A biocide can also optionally be added to the coating solution to control the bioburden level of the coating solution. In one instance, the biocide used can be Biogard, or other similar biocides.

In another optional step, the coated article can include a post-treatment with a lubricant after coating, such as cetylpyridinium chloride (CPC). In another aspect, the coated article can further include a post-treatment with an antifoam agent, as well as other lubricants such as silicone, and/or ammonium salts of alkyl phosphates. In one example, an antifoam agent such as ANTIFOAM 1920 can be provided, manufactured by Dow Corning Corporation. In another example a silicone emulsion such as SM2140, manufactured by Momentive Performance Materials, can be provided which includes polydimethylsiloxane, nonoxynol-20 and laureth-23. In yet another example, ammonium salts of alkyl phosphates such as DarvanX L can be provided, manufactured from Vanderbilt Chemicals, LLC.

Turning to FIG. 1, a flow diagram is shown that illustrates an exemplary embodiment of a process of making a glove material, including the step of coating the glove with the water-based hydrogel blend disclosed herein. At Step 1, a mold or glove former is prepared. The mold is shaped like a hand and dipped with the fingers of the mold pointing downward into a latex polymer. Prior to use, the glove mold can be cleaned by washing and scrubbing the formers.

Once the mold is prepared and cleaned, the glove mold can be further prepared by dipping into a coagulant to coat the glove mold prior to dipping into the latex dispersion being used to form the glove, as shown at Step 2, after which the mold is oven dried at Step 3 at a temperature from about 55° C. to about 60° C. for about 5 minutes.

After the mold is prepared, then the mold can be dipped into the elastomeric latex dispersion being used to form that particular glove, as shown in Step 4. The dipped mold is withdrawn from the latex after a predetermined time has elapsed, and a portion of the latex dispersion forms a layer on the mold. The elastomeric glove as disclosed herein can be produced using any conventional manufacturing methods known in the art. In the embodiment of FIG. 1, the glove is shown as being formed via the coagulant dipping process. In one aspect of the coagulant-dipping process, a former is dipped into a coagulant and then is dipped into the latex dispersion, and is then cured to form a finished article. Alternatively, any other process that is appropriate may be used. These methods utilize dispersions containing the elastomer from which the finished article is to be formed. Preferred elastomers include natural rubber, polyurethane, polybutadiene, polychloroprene (Neoprene), nitrile rubber, block copolymers of styrene and butadiene, block copolymers of styrene and isoprene, and polyisoprene. According to certain aspects, the elastomer can be natural rubber. According to other aspects, the elastomer can be synthetic rubber, and specifically synthetic polyisoprene.

After dipping the glove mold into the latex dispersion, the coated former can be dried at ambient temperature for about 3 minutes (Step 5), followed by a beading step (Step 6), where beading is a process to roll the latex film to form a band near the cuff area. A pre-cure leaching step may be added following the drying and beading of the dipped glove, as in Step 7, where the leaching temperature is from about 65° C. to about 80° C. and the leaching time is about 240 seconds.

In Step 8, the formed glove, still on the glove mold, is dipped into the water-based hydrogel blend to form a coating on the outer surface of the glove, which will later become the inner skin-contacting surface upon glove removal from the mold. The coating composition has a total solids content of about 3.5% to about 4.8%. The temperature of the coating composition at the dipping step is maintained at about 25° C. to about 35° C. and the dipping time of the formed glove into the coating composition is about 12 seconds. The formed glove can still be wet or partially dry upon dipping into the hydrogel blend coating composition; thus, the glove does not need to be completely dry prior to dipping in the coating solution. Notably missing from the flow diagram in FIG. 1 is a chemical priming step prior to dipping the formed glove into the hydrogel blend composition because such a step is not necessary. Although it is possible without the priming, an optional priming step may be added. The process used here where the glove mold can be first dipped into the latex dispersion and then dipped into the hydrogel blend coating without a priming step can be referred to as a "lean dual-dip" process, since an additional step in between is not necessary to prepare the latex to receive the coating and the dual dip can essentially be performed one right after the other, with a short pause between the two dips to allow the first latex layer to dry, if desired. The coating is formed on the glove outer surface (which later becomes the inner, skin-contacting surface) and is cured (Step 9). At the curing step, Step 9, the gloves are vulcanized at about 135° C. for about 20 minutes. At Step 10, calcium carbonate is applied to the formed glove, this is just a light powder to help keep the gloves from sticking together prior to a final rinse or chlorination step, after which the powder is rinsed away.

At Step 11, the glove is then stripped. As the glove is stripped off of the mold it is reversed, such that the coated surface of the glove is now on the interior of the glove, e.g., the glove is removed on an inside-out basis. This allows the coated portion of the glove to come into contact with the skin of the user.

After the gloves are removed a chlorination step may be provided. The gloves of FIG. 1 were chlorinated after formation. First, the coated glove was loaded into a chlorinator where the glove was pre-rinsed twice. An aqueous chlorine solution of about 95 ppm chlorine was then added to the chlorinator. The gloves were tumbled in the chlorinator for about 20 minutes. The chlorinated solution was then neutralized with about 50% sodium hydroxide solution for about 4 minutes. The glove was post-rinsed 5 times for a total elapsed time of about 15 minutes. The glove was then transferred to an extractor to extract excessive water from the glove and then loaded into a cyclone dryer for drying at about 70° C. for about 20 minutes and subsequently cooled by ambient blowing for about 2 minutes.

The dried glove was then loaded into a lubricator (e.g., tumbling washer) for application of a lubrication process. The aqueous lubrication solution comprised of about 0.1090 wt % of cetylpyridinium chloride (CPC), 0.08 wt % of silicone emulsion, 0.014 wt % of antifoam and 0.48 wt % of ammonium salts of alkyl phosphate. The glove was tumbled in the lubricator and sprayed with about 15 liters of lubrication solution and the glove was tumbled for about 19 minutes. The glove was then removed from the lubricator and dried in a cyclone dryer with a heating cycle of about 28 minutes at about 70° C. and a cool down cycle for about 2 minutes.

Although gloves are described in this embodiment, any elastomeric article appropriate for receiving a hydrogel blend coating can be used instead of a glove. In one aspect, the elastomeric article may comprise finger cots, catheters, condoms, probe covers, and other appropriate elastomeric articles.

Figure 5:
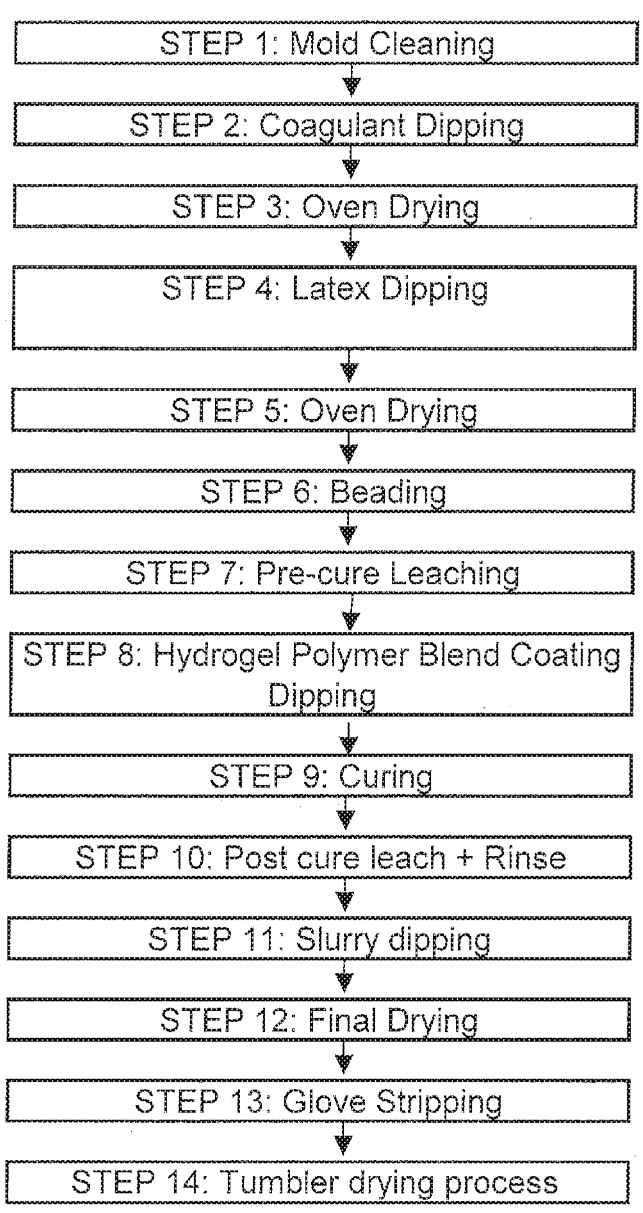
FIG. 5 is a flow diagram of a second exemplary coating process using the water-based hydrogel blend disclosed herein.

Turning to FIG. 5, another flow diagram is shown that illustrates another exemplary embodiment of a process of making a glove material, including the step of coating the glove with the water-based hydrogel blend disclosed herein. At Step 1, a mold or glove former is prepared, such as by cleaning the former. In one example, the glove mold can be cleaned by using rotating brushes such that the mold can pass through these brushes and become cleaned. The mold can also pass through a water tank for additional cleaning.

Once the mold is prepared and cleaned, the glove mold can be further prepared by dipping into a coagulant to coat the glove mold prior to dipping into the latex dispersion being used to form the glove, as shown at Step 2, after which the mold is oven dried at Step 3 at a temperature of about 100° C. for about 20 seconds.

After the mold is prepared, then the mold can be dipped into the elastomeric latex dispersion being used to form that particular glove, as shown in Step 4. The dipped mold is withdrawn from the latex after a predetermined time has elapsed, and a portion of the latex dispersion forms a layer on the mold. The elastomeric glove as disclosed herein can be produced using any conventional manufacturing methods known in the art. In the embodiment of FIG. 5, the glove is shown as being formed via coagulant dipping. In one aspect of the coagulant-dipping process, a former is dipped into a coagulant and then is dipped into the latex dispersion, and is then cured to form a finished article. Any process that is appropriate may be used. Preferred elastomers include natural rubber, and synthetic rubber including polyurethane, polybutadiene, polychloroprene (Neoprene), nitrile rubber, block copolymers of styrene and butadiene, block copolymers of styrene and isoprene, and polyisoprene. According to certain aspects, the elastomer can be natural rubber. According to other aspects, the elastomer can be synthetic rubber, specifically polyisoprene.

After dipping the glove mold into the latex dispersion, the coated former can be dried in an oven at a temperature of about 40° C. for about 20 seconds (Step 5), followed by a beading step (Step 6). A pre-cure leaching step may be added following the drying and beading of the dipped glove, as in Step 7, where the leaching temperature is from about 65° C. to about 80° C. and the leaching time is about 60 seconds.

In Step 8, the formed glove, still on the glove mold, is dipped into the water-based hydrogel blend to form a coating on the outer surface of the glove, which will later become the inner skin-contacting surface upon glove removal from the mold. The coating composition has a total solids content of about 3.5% to about 4.8%. The temperature of the coating composition at the dipping step is maintained at about 25° C. to about 35° C. and the dipping time into the composition is about 12 seconds. The formed glove can still be wet or partially dry upon dipping into the hydrogel blend coating composition; thus, the glove does not need to be completely dry prior to dipping in the coating composition. As in the process flow shown in FIG. 1, also missing from the flow diagram in FIG. 5 is a chemical priming step prior to dipping the formed glove into the hydrogel blend composition because such a step is not necessary. The process of FIG. 5 similarly uses a "lean dual-dip" process. The coating is formed on the glove outer surface (which later becomes the inner, skin-contacting surface) and is cured (Step 9) and followed by a post cure leach and rinse, at Step 10. At the curing step, Step 9, the gloves pass through a series of curing ovens having a temperature in the range of from about 105° C. to about 120° C. The curing time is about 12 minutes.

At Step 11, the coated glove still on the mold is dipped into a slurry. The slurry can comprise, in one aspect, a mixture of a biocide and calcium carbonate. A final drying step is then provided in Step 12, where the coated glove is dried at a temperature of about 50° C. for about 20 seconds.

After the final drying step, the coated glove is stripped off of the glove mold at Step 13. As the glove is stripped off of the mold it is reversed, such that the coated surface of the glove is now on the interior of the glove, e.g., the glove is removed on an inside-out basis. This allows the coated portion of the glove to come into contact with the skin of the user. The removed gloves can be dried once more in a tumbler at a temperature of about 60° C. for about 12 minutes, with a cooling step following for about 8 minutes. After the gloves are removed a chlorination step can be provided, similar to that described in FIG. 1 above.

Another exemplary embodiment can employ the hydrogel blend coating for elastomeric articles by also providing a textured coating or surface to the article being coated. Moreover, the hydrogel blend coated articles, such as a glove, can provide for a tailor-made grip of the glove based on the requirements or preferences of the intended use without compromising donning properties.

In one exemplary aspect, the hydrogel blend coating can be applied to a natural rubber latex article, such as a glove. The hydrogel blend in this aspect can comprise a blend of natural rubber and nitrile added to the hydrogel. The gloves formed with natural rubber can be formed on either a smooth glove mold or a textured glove mold. If gloves are formed using the textured glove mold, this provides the inner surface of the glove, e.g., the mold-contacting surface, with a texture or protrusions on the glove. This mold-contacting surface will later become the outer surface of the glove when it is removed from the former and reversed, thus, providing the outer surface of the glove with an enhanced gripping surface, e.g., a high frictional grip. The gloves may or may not contain a pigment to provide a colored glove, such as, for example a brown colored glove, or the glove can be provided in a white or beige color. In addition, the gloves can have an array of possible thicknesses, as appropriate for its use. For instance, the gloves may be provided with a micro thickness, which in one example can range from about 0.15 mm to about 0.18 mm. In another example, the gloves may be provided with a standard thickness, which in one example may be from about 0.20 mm to about 0.26 mm. In yet another example, the gloves may be provided with a thicker make-up, such as from about 0.30 mm to about 0.37 mm.

In yet another exemplary aspect, the hydrogel blend coating can be applied to a synthetic rubber glove. In one instance it is a polyisoprene glove. In that instance, the hydrogel blend comprises the hydrogel and at least a polyisoprene material and nitrile blended together with the hydrogel to make up the coating composition. Similar to the natural rubber glove above, the polyisoprene gloves can be formed on either a smooth glove mold or a textured glove mold and the gloves may or may not contain a pigment to provide a colored glove, such as, for example a brown colored glove or a white or beige colored glove. Furthermore, the polyisoprene glove can be provided in any thickness appropriate for the use of the glove. The gloves may be provided with a micro thickness, which in one example can range from about 0.15 mm to about 0.18 mm. In another example, the gloves may be provided with a standard thickness, which in one example may be from about 0.20 mm to about 0.26 mm. In yet another example, the gloves may be provided with a thicker make-up, such as from about 0.30 mm to about 0.37 mm.

In the aspect above, where a textured glove having enhanced gripping abilities is desired, to obtain an enhanced grip the gloves may need to be chlorinated with no or low chlorine. The low levels of chlorine helps to maintain and enhance the gripping ability of the final glove product. If a non-coated glove is used, the process of chlorinating the gloves at low chlorine strength will result in poor donnability, since the donning surface (i.e., skin-contacting surface of the glove) is not treated with sufficient chlorine strength. In contrast, a glove treated with the hydrogel blend coating can provide an improved lubricity for donning the glove even with very low or no chlorine. Thus, the coated gloves offer the flexibility to chlorinate the gloves at low chlorine strength and yet maintain the desired grippability of the outer surface of the glove.

The following non-limiting examples illustrate particular embodiments of the coating composition and process for coating as disclosed herein. The examples are not meant to be comprehensive of the entire scope of the coating composition and process for coating.

Example 1

A hydrogel blend coating formulation is provided according to Table 1 below. In particular, the hydrogel is provided at approximately 75% by weight, natural rubber is provided at about 18.6% by weight and nitrile latex is provided at about 6.2% by weight in the hydrogel blend. Additional surfactants and a biocide are also included. The surfactants are added because of the additional elastomer materials in the coating composition, the surfactant can help to blend the natural rubber and nitrile together in solution and effectively help to stabilize the two elastomers in solution. In comparison, a hydrogel-only solution is also provided. The hydrogel only solution was prepared without surfactants because it did not contain any additional elastomeric materials that it needed to stabilize. In addition, the hydrogel only coating cannot support a high amount of lubricant after coating due to not being able to meet the powder content specification requirement as per ASTM standard 3577; this is shown in more detail in Example 8.

TABLE 1

| Coating Composition Make-up for Natural Rubber Substrates | | |
|---|---|---|
| Ingredients | Composition A Hydrogel-Only (% w/w) | Composition B Hydrogel Blend (% w/w) |
| Hydrogel | 100 | 75 |
| Igepal CO630 | 0 | 0.12 |
| Darvan ® WAQ | 0 | 0.05 |
| Nitrile Latex | 0 | 6.21 |
| Natural Rubber Latex | 0 | 18.62 |
| Biogard | 0.03% of total wt. | 0.03% of total wt. |
| Total | 100 | 100 |

The hydrogel blend coating composition has a total solids content in the range of about 3.5% to about 4.7%, unless otherwise indicated in the below tests. Typically, a total solids content of about 4% is targeted. The hydrogel only composition is at about 3% total solids content, unless otherwise indicated in the below tests.

Example 2

The coating formulations prepared in Example 1 were each prepared at three different total solids contents; 3%, 3.5%, and 4% and were tested for coating adhesion to a natural rubber substrate. A natural rubber glove was formed using a process similar to that shown in FIG. 1. A natural rubber glove was then dipped into the three different total solids content prepared for Composition A, and another glove dipped into the three different total solids content prepared for Composition B.

To test the degree of adhesion of the coating on the substrate, a stretch test is performed after the coating has cured on the glove by stretching and pulling at both the finger portion of the glove and the cuff portion of the glove where the glove is stretched from its rest position to a position that is 100% stretched, and it is then released back to its rest position. Once the coated glove is stretched, the tester can use a finger to rub on the coating of the glove to see if the coating flakes off. The gloves are measured on a scale of 1-3, where 1 is no flaking and 3 is a high degree of flaking.

In addition, SEM (scanning electron microscope) scans are also taken of each sample to show the surface morphology of the coated gloves after being stretched. The glove sample is cut to an appropriate size and shape, as specified per ASTM D412, with a die cut to prepare a test specimen used for the SEM test scan. One method for cutting the glove sample as adopted per the ASTM test specification is the dumbbell test specimen. The test specimen is then stretched with a tensiometer to 500% of its original length and held for about one minute before allowing the stretched glove specimen to revert back to its original position.

The coating adhesion tests showed that the hydrogel polymer blend has an improved coating adhesion compared to the hydrogel only coating and the hydrogel blend coating does not flake off of the glove after being stretched. In contrast, the hydrogel only coated glove exhibited a high degree of flaking of the coating off of the final glove product. Test results for the adhesion tests are shown below in Table 2, where Composition A is the hydrogel only coating composition and Composition B is the hydrogel blend coating composition.

TABLE 2

| Stretch Test Data | | |
|---|---|---|
| Total Solids Content (%) | Flake Rating (Composition A) | Flake Rating (Composition B) |
| 3.0% | 3 | 1 |
| 3.5% | 3 | 1 |
| 4.0% | 3 | 1 |

Figure 2B:
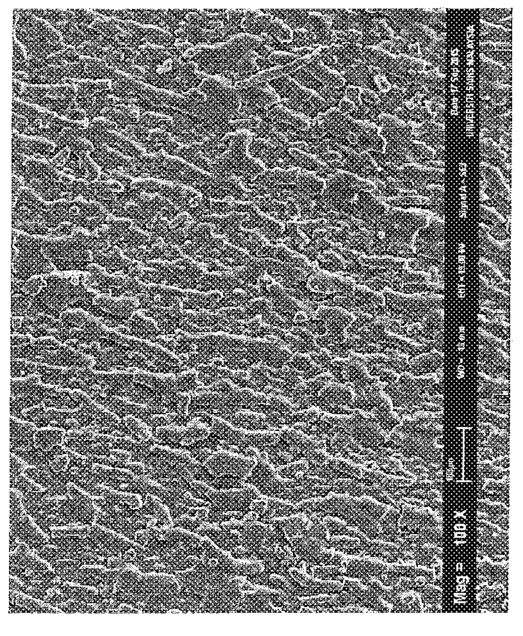
FIG. 2B is a SEM scan at 100× magnification of a hydrogel blend coated glove after stretching the glove, showing the unaffected topical coating surface of the coated glove in the water-based hydrogel blend disclosed herein.
Figure 2A:
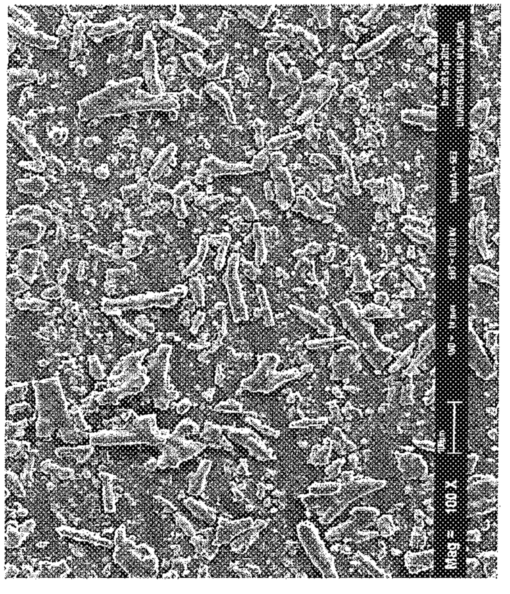
FIG. 2A is a SEM scan at 100× magnification of a hydrogel only coated glove after stretching the glove.

After the gloves were stretched and an observation was made of the flaking, a glove coated with Composition A and a glove coated with Composition B were scanned under a Scanning Electron Microscope (SEM) to observe the effects of stretching and flaking on the glove. FIGS. 2A and 2B show the SEM scan data for these coated gloves at 100× magnification. In FIG. 2A, the glove coated with Composition A (i.e., hydrogel-only coating) is shown after it is stretched. It can be seen that there are several uncoated areas that became exposed due to the coating flaking off after the coated glove was stretched. In contrast, in FIG. 2B, the glove coated with Composition B (i.e., hydrogel blend coating) is shown after it is stretched and it shows a homogenous and completely coated surface morphology. Since no flaking of the coating was exhibited with the gloves coated with Composition B, there are no exposed uncoated surfaces of the glove in FIG. 2B.

Example 3

Another set of coating adhesion tests was performed using coating compositions having differing amounts of elastomeric materials added to the hydrogel. Table 3 below indicates the amounts of the ingredients used in the different compositions tested.

TABLE 3

| Test Solution Make-up | | | | | | |
|---|---|---|---|---|---|---|
| Ingredients | Composition A Hydrogel-Only Solution (% w/w) | Composition C Hydrogel Blend Solution (% w/w) | Composition D Hydrogel Blend Solution (% w/w) | Composition E Hydrogel Blend Solution (% w/w) | Composition F Hydrogel Blend Solution (% w/w) | Composition G Hydrogel Blend Solution (% w/w) |
| Hydrogel | 100 | 90 | 75 | 75 | 75 | 75 |
| Nitrile Latex | 0 | 2.5 | 12.5 | 19 | 25 | 0 |
| Natural Rubber Latex | 0 | 7.5 | 12.5 | 6 | 0 | 25 |

Similar to Example 2, a natural rubber glove was formed and dipped into its respective coating composition. Once the coating was cured onto the glove the stretch tests were performed as described in Example 2 to measure the degree of coating adhesion. Results of the stretch test are shown below in Table 4.

TABLE 4

| Stretch Test Data | | | |
|---|---|---|---|
| Coating Composition | Flake Result at 3% Total Solids Content | Flake Result at 3.5% Total Solids Content | Flake Result at 4% Total Solids Content |
| Composition A | 3 | 3 | 3 |
| Composition C | 3 | 3 | 3 |
| Composition D | 1 | 1 | 1 |
| Composition E | 1 | 1 | 1 |
| Composition F | 3 | 3 | 3 |
| Composition G | 2 | 2 | 3 |

The results of the stretch test show that even at equal amounts of the natural rubber and nitrile latex the coating still exhibits excellent adhesion to the glove. Likewise, at a coating having greater nitrile latex content versus natural rubber latex, the coating adhesion is still excellent. This shows that whether the nitrile latex is present in a greater quantity or the natural rubber latex is present in a greater quantity does not affect the performance and properties of the coating adherence to the glove product; thus, the elastomeric materials can be present in any ratio. In particular, the glove base material was a natural rubber latex material and it does not matter whether the natural rubber in the hydrogel blend is present in a major amount or a minor amount in the coating composition.

In contrast, the hydrogel only coating had a high degree of flaking as did a hydrogel blend coating that had about 90% hydrogel and only 10% elastomeric blend comprising natural rubber and nitrile. Similarly, Compositions F and G which contained only one elastomeric material and hydrogel at about 75% showed a high degree of flaking at a total solids content of 3%, 3.5%, and 4%.

The total solids content did not seem to affect the results for the hydrogel blend coatings. However, the stretch test did show that at a higher solid content of about 4% the hydrogel only coating exhibited a high degree of flaking and that adherence to the glove was not good. In contrast, the hydrogel blend of Composition B (from Example 2), Composition D and Composition E exhibited excellent adherence even at high solids content of 4%.

An additional stretch test was run utilizing solution D at about 4.7% total solids content which also yielded a result of 1, or no flaking of the coating at the higher solids content level with equal amounts of nitrile and natural rubber and about 75% hydrogel. Thus, a hydrogel blend having about 75% hydrogel and the remainder of the composition being an elastomeric blend, regardless of the amounts of each individual elastomeric material within the blend, exhibits excellent adherence properties to the glove and upon stretching the glove, no flaking is exhibited at all three total solids content levels tested. Therefore, a glove article can be coated with the hydrogel blend composition at high solids content without any flaking and exhibiting excellent coating adhesion to the rubber substrate.

Example 4

A hydrogel blend coating formulation is provided according to Table 5 below. In particular, the hydrogel is provided at approximately 85% by weight, synthetic polyisoprene compound is provided at about 7.5% by weight and nitrile latex is provided at about 7.5% by weight in the hydrogel blend. Additional surfactants and a biocide are also included. The surfactants are added because of the additional elastomer materials in the coating composition, the surfactant can help to blend the synthetic polyisoprene compound and nitrile together in solution and effectively help to stabilize the two elastomers in solution. In comparison, a hydrogel-only solution is also provided. The hydrogel only solution was prepared without surfactants because it did not contain any additional elastomeric materials that it needed to stabilize. In addition, the hydrogel only coating cannot support a high amount of lubricant after coating due to not being able to meet the powder content specification requirement as per ASTM standard 3577; this is shown in more detail in Example 8.

TABLE 5

| Coating Composition make-up for Synthetic Rubber Substrates | | |
|---|---|---|
| Ingredients | Composition A Hydrogel-Only (% w/w) | Composition H Hydrogel Blend (% w/w) |
| Hydrogel | 100 | 85 |
| Igepal CO630 | 0 | 0.12 |
| Darvan ® WAQ | 0 | 0.05 |
| Nitrile Latex | 0 | 7.5 |
| Synthetic Polyisoprene compound | 0 | 7.5 |
| Biogard | 0.03% of total wt. | 0.03% of total wt. |
| Total | 100 | 100 |

The hydrogel blend coating composition has a total solids content in the range of about 3.5% to about 4.5%, unless otherwise indicated in the below tests. Typically, a total solids content of about 4% is targeted. The hydrogel only composition is at about 3% total solids content, unless otherwise indicated in the below tests.

Example 5

The coating formulations prepared in Example 4 were each prepared at three different total solids contents; 3%, 3.5%, and 4% and were tested for coating adhesion to a synthetic polyisoprene substrate. A synthetic polyisoprene glove was formed using a process similar to that shown in FIG. 1. A synthetic polyisoprene glove was then dipped into the three different total solids content prepared for Composition A, and another glove dipped into the three different total solids content prepared for Composition H.

To test the degree of adhesion of the coating on the substrate, a stretch test is performed after the coating has cured on the glove by stretching and pulling at both the finger portion of the glove and the cuff portion of the glove where the glove is stretched from its rest position to a position that is 100% stretched, and it is then released back to its rest position. Once the coated glove is stretched, the tester can use a finger to rub on the coating of the glove to see if the coating flakes off. The gloves are measured on a scale of 1-3, where 1 is no flaking and 3 is a high degree of flaking.

In addition, SEM (scanning electron microscope) scans are also taken of each sample to show the surface morphology of the coated gloves after being stretched. The glove sample is cut to an appropriate size and shape, as specified per ASTM D412, with a die cut to prepare a test specimen used for the SEM test scan. One method for cutting the glove sample as adopted per the ASTM test specification is the dumbbell test specimen. The test specimen is then stretched with a tensiometer to 500% of its original length and held for about one minute before allowing the stretched glove specimen to revert back to its original position.

The coating adhesion tests showed that the hydrogel polymer blend has an improved coating adhesion compared to the hydrogel only coating and the hydrogel blend coating does not flake off of the glove after being stretched. In contrast, the hydrogel only coated glove exhibited a high degree of flaking of the coating off of the final glove product. Test results for the adhesion tests are shown below in Table 6, where Composition A is the hydrogel only coating composition and Composition H is the hydrogel blend coating composition.

TABLE 6

| Stretch Test Data | | |
|---|---|---|
| Total Solids Content (%) | Flake Rating (Composition A) | Flake Rating (Composition H) |
| 3.00% | 2.67 | 1 |
| 3.50% | 2 | 1 |
| 4.00% | 2 | 1.33 |

Figure 6B:
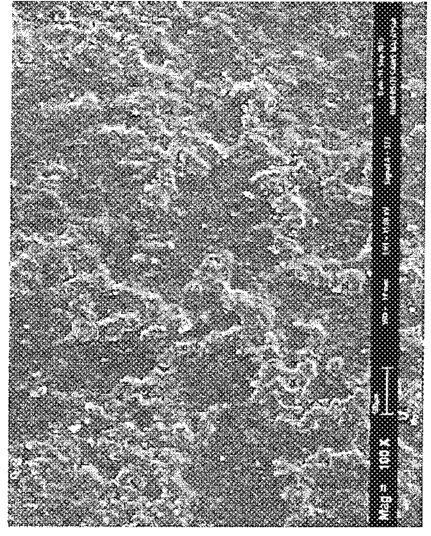
FIG. 6B is a SEM scan at 100× magnification of a hydrogel only coated polyisoprene glove, without stretching, that depicts the topical coating surface of the glove after dipping in the water-based hydrogel alone.
Figure 6A:
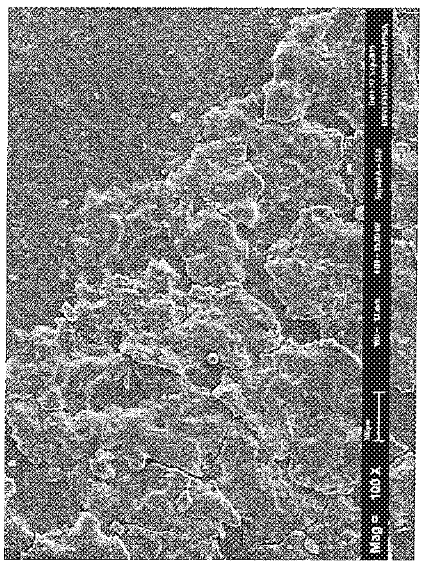
FIG. 6A is a SEM scan of a polyisoprene glove coated with a hydrogel-polyisoprene-nitrile blend, shown at 100× magnification.

After the gloves were stretched and an observation was made of the flaking, a glove coated with Composition A and a glove coated with Composition H were scanned under a Scanning Electron Microscope (SEM) to observe the effects of stretching and flaking on the glove. FIGS. 6A and 6B show the SEM scan data for these coated gloves at 100× magnification. In FIG. 6B, the glove coated with Composition A (i.e., hydrogel-only coating) is shown after it is stretched. It can be seen that there are several uncoated areas that became exposed due to the coating flaking off after the coated glove was stretched. In contrast, in FIG. 6A, the glove coated with Composition H (i.e., hydrogel blend coating) is shown after it is stretched and it shows a homogenous and completely coated surface morphology. Since no flaking of the coating was exhibited with the gloves coated with Composition H, there are no exposed uncoated surfaces of the glove in FIG. 6A.

Example 6

Another set of coating adhesion tests was performed using coating compositions having differing amounts of elastomeric materials added to the hydrogel. Table 7 below indicates the amounts of the ingredients used in the different compositions tested.

TABLE 7

| Test Solution Make-up | | | | | | |
|---|---|---|---|---|---|---|
| Ingredients | Composition A Hydrogel-Only Solution (% w/w) | Composition I Hydrogel Blend Solution (% w/w) | Composition J Hydrogel Blend Solution (% w/w) | Composition K Hydrogel Blend Solution (% w/w) | Composition L Hydrogel Blend Solution (% w/w) | Composition M Hydrogel Blend Solution (% w/w) |
| Hydrogel | 100 | 92 | 85 | 85 | 85 | 85 |
| Nitrile Latex | 0 | 6 | 11 | 4 | 0 | 15 |
| Synthetic Polyisoprene compound | 0 | 2 | 4 | 11 | 15 | 0 |

Similar to Example 5, a synthetic polyisoprene glove was formed and dipped into its respective coating composition. Once the coating was cured onto the glove the stretch tests were performed as described in Example 5 to measure the degree of coating adhesion. Results of the stretch test are shown below in Table 8.

TABLE 8

| Stretch Test Data | | | |
|---|---|---|---|
| Coating Composition | Flake Result at 3% Total Solids Content | Flake Result at 3.5% Total Solids Content | Flake Result at 4% Total Solids Content |
| Composition A | 2 | 2 | 2.67 |
| Composition I | 2.5 | 2 | 2.67 |
| Composition J | 1 | 1.33 | 1.67 |
| Composition K | 1 | 2 | 1 |
| Composition L | 2 | 2 | 2.33 |
| Composition M | 3 | 2.67 | 2.5 |

The results of the stretch test show that even at non-equal amounts of the synthetic polyisoprene and nitrile latex the coating still exhibits excellent adhesion to the glove. Likewise, at a coating having greater nitrile latex content versus synthetic rubber latex, the coating adhesion is still excellent. This shows that whether the nitrile latex is present in a greater quantity or the synthetic rubber latex is present in a greater quantity does not affect the performance and properties of the coating adherence to the glove product; thus, the elastomeric materials can be present in any ratio. In particular, the glove base material was a synthetic rubber latex material and it does not matter whether the synthetic rubber in the hydrogel blend is present in a major amount or a minor amount in the coating composition.

In contrast, the hydrogel only coating had a high degree of flaking as did a hydrogel blend coating that had about 92% hydrogel and only 8% elastomeric blend comprising synthetic rubber and nitrile. Similarly, Compositions and which contained only one elastomeric material and hydrogel at about 85% showed a high degree of flaking, The total solids content did not seem to affect the results for the hydrogel blend coatings. However, the stretch test did show that at a higher solids content of about 4% the hydrogel only coating exhibited a high degree of flaking and that adherence to the glove was not good. In contrast, the hydrogel blend of Composition H (from Example 5), Composition J and Composition K exhibited excellent adherence even at high solids content of 4%.

Example 7

A mechanical stability test (MST) was performed to determine the mechanical stability of the coating compositions. The MST is a measure of the coating compositions ability to withstand high speed agitation without coagulating. It is determined by subjecting the coating composition, which has first been strained through a 180-μm sieve, to the action of a high speed stirrer. Approximately 50 grams of the strained solution is weighed out and placed into a test bottle. The bottle is placed onto the tester and is agitated at about 14,000±200 rpm for 30 minutes. The temperature is measured and recorded every 10 minutes to make sure that the coating composition temperature does not exceed about 60° C. at any time during the test. The agitated coating composition is then strained through a 180 μm filter and the coagulum obtained on the filter is then dried in the oven at about 100° C. until the weight of the coagulum is constant. The percentage of coagulum that remains on the filter after filtration is then recorded. The higher the percentage of coagulum that remains on the filter indicates poor stability of the coating composition.

Seven different coating formulations were tested: Composition A and Composition B as prepared in Example 1, Compositions F and G as shown in Example 3, Composition H as prepared in Example 4, and Compositions L and M as shown in Example 6. The coatings were prepared at 5% total solids content. The MST was performed by initially subjecting the coating compositions to a heating step at about 40° C. with continuous stirring throughout the test for the total 3 day evaluation, with measurements taken for 1, 2, and 3 days. The results recorded are shown below in Tables 9 & 10.

TABLE 9

Coating Stability Test
Results with natural rubber elastomer

| 5% Total Solids Content Compositions | Percent Coagulum | | |
|---|---|---|---|
| Composition Tested | Day 1 | Day 2 | Day 3 |
| Composition A | 0.128 | 0.144 | 0.117 |
| Composition B | 0.025 | 0.026 | 0.026 |
| Composition F | 0.123 | 0.207 | 0.270 |
| Composition G | 0.300 | 0.101 | 0.005 |

TABLE 10

Coating Stability Test
Results with synthetic rubber elastomer

| 5% Total Solids Content Compositions | Percent Coagulum | | |
|---|---|---|---|
| Composition Tested | Day 1 | Day 2 | Day 3 |
| Composition A | 0.53 | 0.56 | 0.42 |
| Composition H | 0.29 | 0.3 | 0.28 |
| Composition L | 0.35 | 0.38 | 0.34 |
| Composition M | 0.7 | 0.84 | 0.99 |

Based on the results obtained, it can be seen that the hydrogel only coating composition (Composition A) is much less thermally and mechanically stable than the hydrogel blend coating compositions (Compositions B and H). The coating compositions (F, G, L, and M) that contained only one elastomeric material in the blend also had poor stability showings. Therefore, the hydrogel blend composition having two different elastomeric materials at a high solids content of 5% showed good thermal and mechanical stability in solution.

The Mechanical Stability Test as described in the previous example was also performed on compositions with added stabilizer.

TABLE 11

Compositions with stabilizer

| Ingredients | Composition A Hydrogel-Only (% w/w) | Composition N (Compound A + Stabilizer) Hydrogel-Only with Stabilizer (% w/w) | Composition B Nobel Blend with Stabilizer (% w/w) |
|---|---|---|---|
| Hydrogel | 100 | 100 | 75 |
| Igepal CO630 | 0 | 0.12 | 0.12 |
| Darvan ® WAQ | 0 | 0.05 | 0.05 |
| Nitrile Latex | 0 | 0 | 6.21 |
| Cold Cure Compound Latex | 0 | 0 | 18.62 |
| Synthetic Polyisoprene compound | 0 | 0 | 0 |
| Total | 100 | 100 | 100 |

These compositions were tested in the MTS test.

TABLE 12

Results of added stabilizer

| 5% Total Solids Content Compositions | Percent Coagulum | | |
|---|---|---|---|
| Composition Tested | Day 1 | Day 2 | Day 3 |
| Composition A | 0.128 | 0.144 | 0.117 |
| Composition N (A + Stabilizer) | 0.362 | 0.27 | 0.218 |
| Composition B + Stabilizer | .037 | .0138 | .0094 |

Addition of Igepal CO630 and Darvan WAQ did not enhance the coating stability of Nobel-only coating (Composition A). However, the addition of the same stabilizers increased the stability of Composition B dramatically after 3 days, to a low value of 0.0094.

Example 8

The coating samples of Compositions A and B were each treated with a lubricant solution on the coated natural rubber article as shown below in Table 12. Each of the gloves were first chlorinated at about 95 ppm chlorine and then lubricated with the lubricant solution of Table 13 by application via a spraying process. The majority of the lubricant solution comprises water with Darvan® L in the next greatest amount after the water, where Darvan® L is the tradename for a surfactant that comprises ammonium salts of alkyl phosphates, obtained from Vanderbilt Chemicals, LLC. In addition, the lubricant CPC (cetylpyridinium chloride) is added, an antifoam agent, such as Antifoam 1920 manufactured by Dow Corning Corporation, and a silicone emulsion, such as Silicone SM2140 manufactured by Momentive Performance Materials.

TABLE 13

| Lubricant Formulation | |
|---|---|
| Ingredients | Percent |
| Soft Water | 99.325 |
| CPC | 0.109 |
| Antifoam 1920 | 0.014 |
| Silicone SM2140 | 0.080 |
| Darvan ® L | 0.480 |
| Total | 100 |

To measure the acceptability of the gloves sprayed with additional lubricant, the powder content of the gloves is measured. In order to be acceptable, the powder content of the gloves must be low, at about less than 2 mg/glove. The powder content of the glove is measured to determine the powder or particulate that remains on the glove after a chlorination process, if used, or after the final process step. Per the requirement in ASTM 3577, a powder-free glove is one that contains less than 2 mg/glove of powder content. To test the powder content of the coated and sprayed gloves, the gloves are put into a beaker with water, the beaker is shaken and the water is filtered to measure the residual powder content that came off of the gloves. The final results are shown in Table 14 below. Two sample sets were tested and are shown in Table 14 for each glove type, where five pieces of gloves were used to achieve one powder content data point for one sample set.

TABLE 14

| Residual Powder Content Test | | |
|---|---|---|
| Sample | Hydrogel-only (Composition A) coated gloves | Hydrogel blend (Composition B) coated gloves |
| Powder Content (mg/glove) - Sample 1 | 3.44 | 0.34 |
| Powder Content (mg/glove) - Sample 2 | 4.22 | 0.38 |

It can be seen from the powder content test that the addition of a lubricant, even one containing about 0.1% CPC provides a high and unacceptable level of residual powder on the glove coated with only hydrogel and treated with lubricant. The hydrogel blend glove can be treated with the lubricant CPC at 0.1% and does not show significant powder content on the glove. Thus, gloves coated with the hydrogel blend coating composition are able to be treated with a higher level of CPC lubricant as compared to the hydrogel only coated gloves.

Example 9

Wet coefficient of friction (COF) testing was done to determine glove donnability following ASTM D1894. Coefficient of friction is defined in this test method as the ratio of the force required to move one surface over another to the total force applied normal to those surfaces. The lower the value, the less friction between the two surfaces. Thus low COF value indicates better donnability.

The ASTM D1894 test method, specifically for wet COF, covers determination of the coefficients of starting and sliding friction of glove film when sliding over itself or other metal plate at wet conditions. The procedure permits the use of a moving sled (wrapped with glove film) with a stationary plane.

A square film (glove) specimen, flat and free of defects, that is to be attached to the sled (a metal block 63.5 mm (2.5 in.) square by approximately 6 mm (0.25 in.) thick with a suitable eye screw fastened in one end) is cut approximately 120 mm (4½ in.) each side. The standard conditioning cycle for the specimens shall be 24 hours at standard laboratory conditions of 23±2° C. (73.4±3.6° F.) and 50±5% relative humidity. If these temperatures and humidity conditions cannot be met, the samples shall be conditioned for a minimum of 24 hours in the same room as the testing equipment. The test apparatus is assembled according to FIG. 1(*c*) in ASTM D1894 and the force measuring device is calibrated using the manufacturer's instructions. The glove sample to be tested is then placed a smooth clean surface and the sled is placed in the approximate center of the sample. The edges of the film are folded over the top of the sled and secured using adhesive tape making sure that the film on the bottom of the sled is not stretched or wrinkled. The testing plane (a polished metal sheet approximately 150 by 300 by 1 mm) is cleaned using isopropyl alcohol or other suitable cleaning agent. For wet testing the plane is sprayed with water. The sled with the sample is attached to the cable used to pull the sled during the test procedure. The sled is then placed in position on the horizontal plane. The positioning of the sled shall be such that the length of the sled, the adjacent length of the cable, and the long dimension of the plane are parallel. The drive mechanism is started using a power operate source that pulls at a uniform speed of 150+/−mm/min. As a result of the frictional force between the contacting surfaces, no immediate relative motion may take place between the sled and the moving plane until the pull on the sled is equal to, or exceeds, the static frictional force acting at the contact surfaces. This initial, maximum reading is the force component of the static coefficient of friction. Any visual average reading during a run of approximately 130 mm (5 in.) while the surfaces are sliding uniformly over one another should also be recorded. This is equivalent to the kinetic force required to sustain motion between the surfaces and normally is lower than the static force required to initiate motion. After sled has traveled over 130 mm (5 in.) the apparatus is stopped. The kinetic coefficient of friction is calculated with the formula $\mu k = Ak/B$, where Ak=average scale reading obtained during uniform sliding of and the film, grams, and B=sled weight, grams.

A blend of 75% hydrogel, 19% natural rubber, and 6% Nitrile at 3 different TSC was tested in 5 samples. The mean is shown in Table 15 and the run data is shown in Table 16.

TABLE 15

| Summary of wet coefficient of friction results at different TSC. | | | |
|---|---|---|---|
| | Nobel/CC/Nitrile (75/19/6) at 7% TSC | Nobel/CC/Nitrile (75/19/6) at 4% TSC | Nobel/CC/Nitrile (75/19/6) at 2% TSC |
| Wet COF | 0.05 | 0.08 | 0.11 |

TABLE 16

| Wet COF testing raw data | | | |
|---|---|---|---|
| Wet COF | Coating TSC | | |
| Sample Tested | 7% | 4% | 2% |
| Sample 1 | 0.06 | 0.06 | 0.12 |
| Sample 2 | 0.03 | 0.1 | 0.07 |
| Sample 3 | 0.04 | 0.06 | 0.13 |
| Sample 4 | 0.12 | 0.08 | 0.11 |
| Sample 5 | 0.01 | 0.11 | 0.11 |
| Mean | 0.05 | 0.08 | 0.11 |

The Wet COF testing shows that the higher level of coating produces gloves with a lower Wet COF, or increased donnability. The ability of the hydrogel blend to be coated higher without flaking results, therefore, results in increased donnability.

Example 10

Coated gloves were evaluated via a scanning electron microscope (SEM) to show the surface morphology of a coated glove after formation and curing. Four samples were prepared and tested; Composition A, Composition B, Composition F and Composition G from previous examples. Natural rubber gloves were formed and then coated, where each glove was coated with a different solution from one of the four. The coated gloves were then examined under a microscope and an SEM scan was taken at 100× magnification, these results are shown in FIGS. 3A-3D.

Figure 3B:
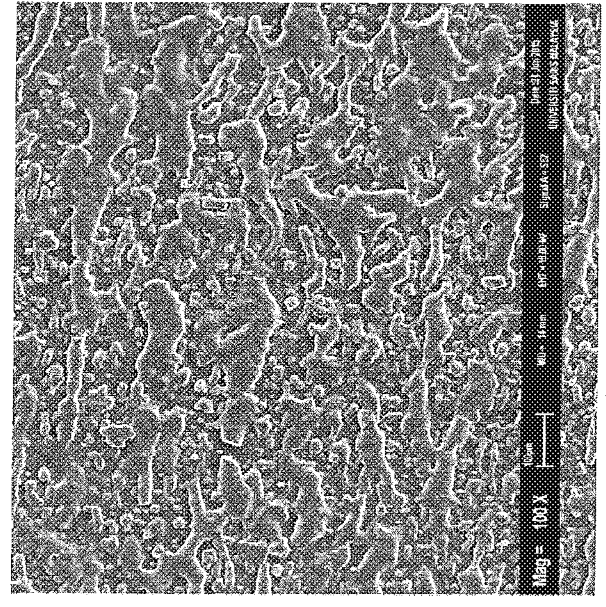
FIG. 3B is a SEM scan at 100× magnification of a hydrogel blend coated glove, without stretching, that depicts the topical coating surface of the glove after dipping in the water-based hydrogel blend composition.
Figure 3A:
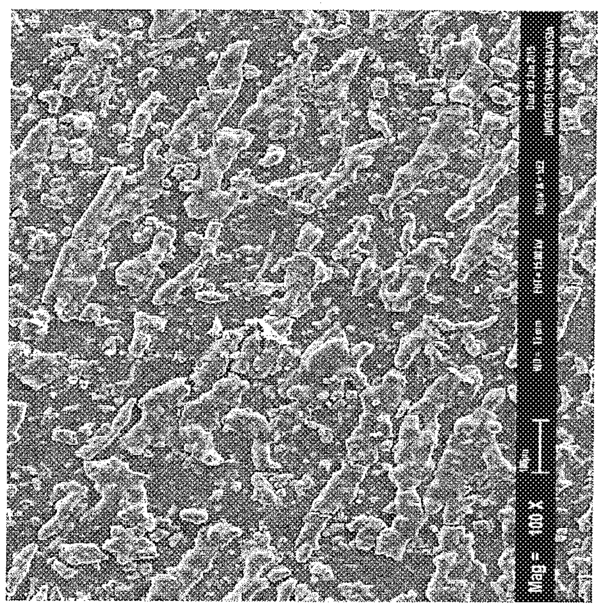
FIG. 3A is a SEM scan at 100× magnification of a hydrogel only coated glove, without stretching, that depicts the topical coating surface of the glove after dipping in the water-based hydrogel alone.

In turning to FIG. 3A, the hydrogel only coating was applied to the glove (i.e., Composition A). The segments that appear throughout the scan are surfaces that have been coated. The gaps or spaces between those segments represent uncoated surface area of the glove. In comparison to FIG. 3B, which represents the hydrogel blend coating (i.e., Composition B), it can be seen that there are significantly more spaces or uncoated surfaces in the scan of FIG. 3A than in 3B. In FIG. 3B there are more continuous patches of the coating segments seen in the scan, which represents a more continuous coating pattern on the glove.

Figure 3D:
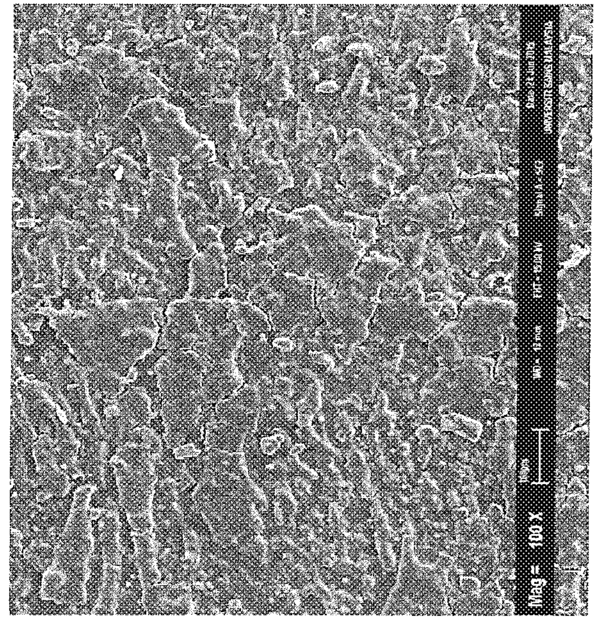
FIG. 3D is a SEM scan at 100× magnification of a single elastomer-hydrogel blend coated glove.
Figure 3C:
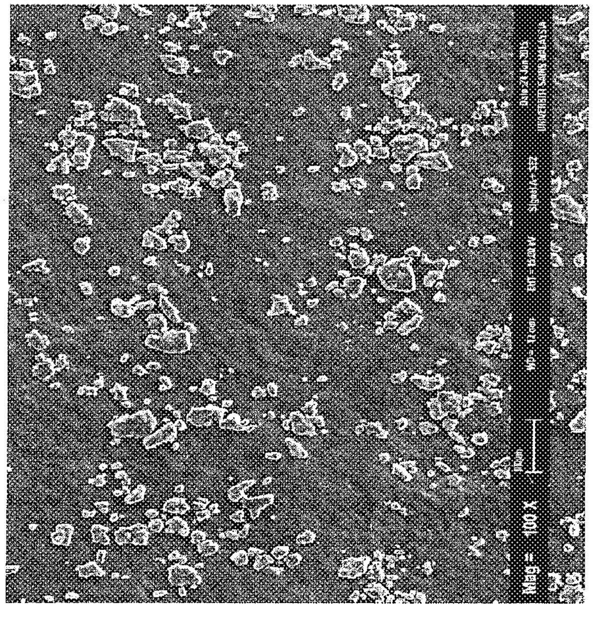
FIG. 3C is a SEM scan at 100× magnification of a single elastomer-hydrogel blend coated glove.

Turning to FIGS. 3C and 3D, these represent the scans for gloves containing a one elastomer-hydrogel blend. In FIG. 3C, a scan of a coated glove coated with hydrogel and natural rubber only (i.e., Composition F) is shown. It can be seen from this scan that there is little coated surface. In FIG. 3D, a scan of a glove coated with hydrogel and nitrile only (i.e., Composition G) is shown. It can be seen that although a majority of the glove surface was coated, it is rather flat as compared to the hydrogel blend and does not have the micro-ridges that help with improved donning that are noticeable in a blend of at least two elastomeric materials. The SEM scans show that the scan of FIG. 3B, containing the hydrogel blend coating, has a unique surface morphology that creates a glove that is coated over a greater surface area than any of the other three coating compositions tested and having a unique surface morphology with surface ridges. In particular, this continuous coating with the hydrogel blend creates an internal tackiness that helps to facilitate donning of the glove.

Example 11

Coated synthetic polyisoprene gloves were tested for surface morphology using SEM scans. A polyisoprene glove was made using a similar coagulant dipping process as shown in FIG. 1 for natural rubber gloves. Once the glove was dipped into the polyisoprene latex, it was dipped into the coating composition and then cured. There were three coating compositions tested on the polyisoprene gloves; a hydrogel only composition and two hydrogel-polyisoprene-nitrile blends. The first hydrogel-polyisoprene-nitrile blend was made using about 75% hydrogel and about 6% polyisoprene, with the remainder of the solution comprising nitrile latex at about 19%. The second hydrogel-polyisoprene-nitrile blend was made using about 85% hydrogel and about 7.5% polyisoprene, with the remainder of the solution comprising nitrile latex at about 7.5%. Upon coating the gloves and curing, the gloves were scanned under SEM to determine the surface morphology and the results can be seen in FIGS. 4A-4B, 6A-6B, 7A-7B, and 8A-8B.

Figure 4B:
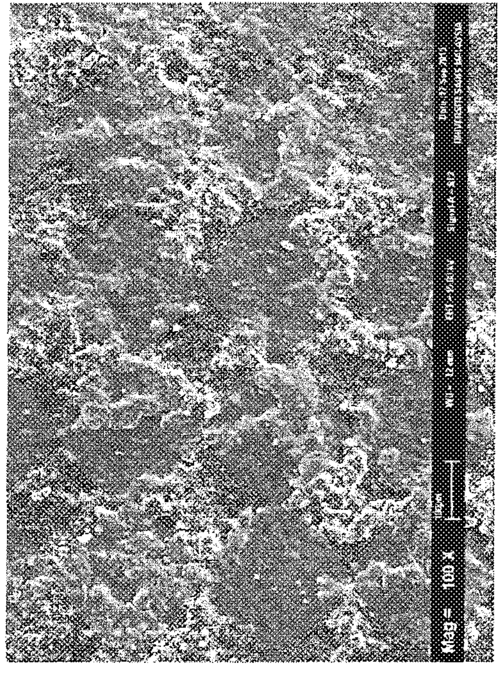
FIG. 4B is a SEM scan of a polyisoprene glove coated with a hydrogel-only coating, shown at 100× magnification.
Figure 4A:
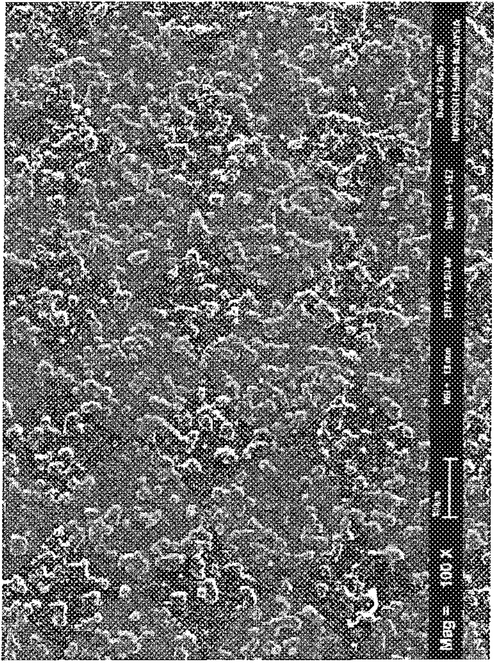
FIG. 4A is a SEM scan of a polyisoprene glove coated with a hydrogel-polyisoprene-nitrile blend, shown at 100× magnification.

The polyisoprene glove coated with the first hydrogel-polyisoprene-nitrile blend was evaluated at 100× magnification (FIG. 4A). The results show that the hydrogel blend on the polyisoprene similarly has a unique surface morphology with micro ridges that covers a large surface area of the glove. In contrast, the polyisoprene glove coated with hydrogel only shows a flat surface on the glove. The hydrogel only coated polyisoprene gloves were also evaluated at 100× magnification (FIG. 4B). In FIG. 4B, the surface of the glove shows not only a flatter surface than the glove in FIG. 4A, but it shows many gaps or spaces that represent uncoated surfaces on the glove.

Figure 7B:
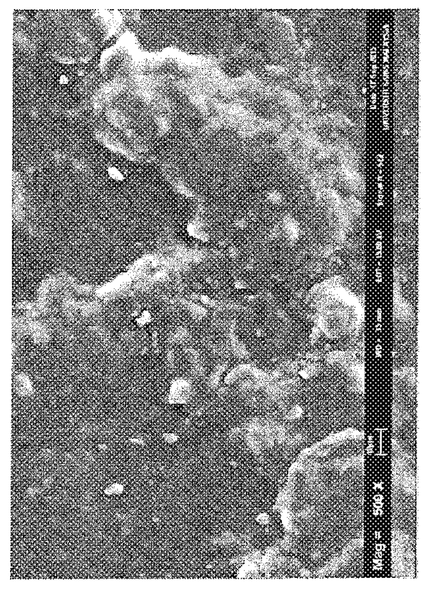
FIG. 7B is a SEM scan at 500× magnification of a hydrogel only coated polyisoprene glove, without stretching, that depicts the topical coating surface of the glove after dipping in the water-based hydrogel alone.
Figure 7A:
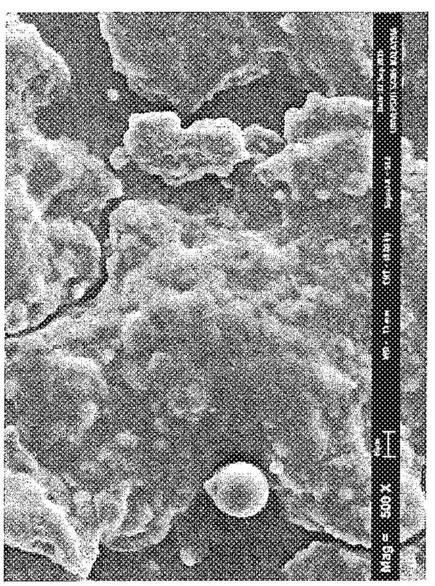
FIG. 7A is a SEM scan of a polyisoprene glove coated with a hydrogel-polyisoprene-nitrile blend, shown at 500× magnification.
Figure 8B:
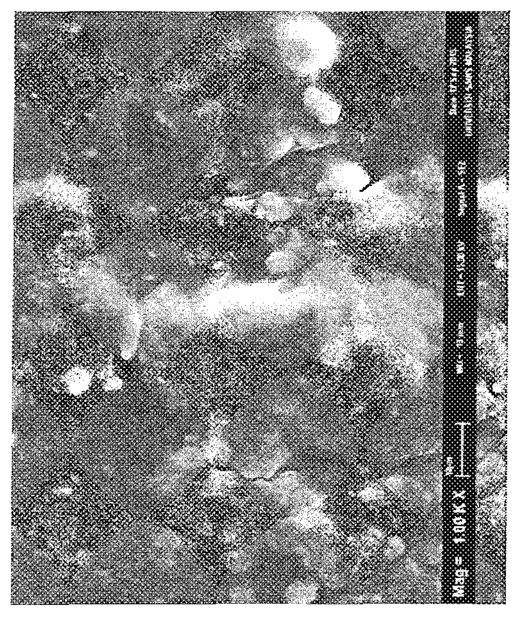
FIG. 8B is a SEM scan at 1000× magnification of a hydrogel only coated polyisoprene glove, without stretching, that depicts the topical coating surface of the glove after dipping in the water-based hydrogel alone.
Figure 8A:
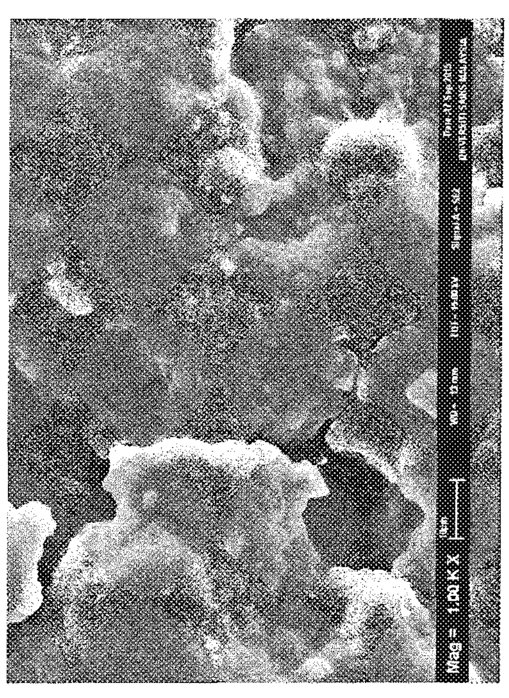
FIG. 8A is a SEM scan of a polyisoprene glove coated with a hydrogel-polyisoprene-nitrile blend, shown at 1000× magnification.

The polyisoprene glove coated with the second hydrogel-polyisoprene hydrogel blend was also evaluated at 100× (FIG. 6A), 500× (FIG. 7A) and 1000× (FIG. 8A). The hydrogel only coated polyisoprene gloves were also evaluated at 100× (FIG. 6B), 500× (FIG. 7B) and 1000× (FIG. 8B) for comparison. The results also show that the hydrogel blend on the polyisoprene similarly has a unique surface morphology with micro ridges that covers a large surface area of the glove. In contrast, the polyisoprene glove coated with hydrogel only shows a flat surface on the glove. In FIGS. 6B, 7B and 8B, the surface of the glove shows not only a flatter surface than the glove in FIGS. 6A, 7A, and 8A, but it shows many gaps or spaces that represent uncoated surfaces on the glove.

Thus, it can be seen that even with a different elastomeric article, i.e., one made from polyisoprene, the hydrogel only coating does not coat as large of a surface area as the hydrogel-polyisoprene-nitrile blend. Moreover, the hydrogel-polyisoprene-nitrile blend still shows a unique surface morphology that aids in providing improved donnability even with a different blend of elastomers.

For purposes of this disclosure, certain aspects, advantages, and novel features are described herein. It is to be understood that not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein. Moreover, while illustrative embodiments have been described herein, the scope of any and all embodiments having equivalent elements, modifications, omissions, combinations (e.g., of aspects across various embodiments), adaptations and/or alterations as would be appreciated by those in the art based on the present disclosure. The limitations in the claims are to be interpreted broadly based on the language employed in the claims and not limited to the examples described in the present specification or during the prosecution of the application, which examples are to be construed as non-exclusive. Further, the actions of the disclosed processes and methods may be modified in any manner, including by reordering actions and/or inserting additional actions and/or deleting actions. It is intended, therefore, that the specification and examples be considered as illustrative only, with a true scope and spirit being indicated by the claims and their full scope of equivalents.

What is claimed is:

1. A method of making a coating, comprising:

combining a water-based hydrogel polymer, a first elastomeric material, and a second elastomeric material to form a coating formulation, wherein the coating formulation does not contain any added solvents, and wherein the second elastomeric material is nitrile latex.

2. The method of claim 1, wherein the water-based hydrogel polymer is present in an amount from about 50% to about 99% by weight in the coating formulation.

3. The method of claim 1, wherein the first elastomeric material is natural rubber latex.

4. The method of claim 1, wherein the first elastomeric material is polyisoprene latex.

5. The method of claim 1, wherein the water-based hydrogel polymer is present in an amount from about 50% to about 90% by weight in the coating formulation.

6. The method of claim 1, wherein the water-based hydrogel polymer is present in an amount from about 75% to about 85% of the coating formulation.

7. The method of claim 1, wherein the first elastomeric material is present in an amount from about 0.5% to about 37% by weight of the coating formulation.

8. The method of claim 1, wherein the second elastomeric material is present in an amount from about 0.5% to about 25% by weight of the coating formulation.

9. The method of claim 1, wherein the second elastomeric material is present in an amount from about 6% to about 19% by weight of the coating formulation.

10. The method of claim 1, wherein the first elastomeric material is present in an amount from about 6% to about 19% by weight of the coating formulation.

11. The method of claim 1, wherein the first elastomeric material is present in an amount from about 4% to about 11% by weight of the coating formulation.

12. The method of claim 1, wherein the second elastomeric material is present in an amount from about 4% to about 11% by weight of the coating formulation.

13. The method of claim 1, wherein the first elastomeric material and the second elastomeric material are each present in an amount of about 7.5% by weight of the coating formulation.

14. The method of claim 1, wherein the coating formulation has a total solids content between about 3% and about 7%.

15. A coating formulation, comprising:

a water-based hydrogel polymer, a first elastomeric material, and a second elastomeric, wherein the coating formulation does not contain any added solvents, and wherein the second elastomeric material is nitrile latex.

16. An elastomeric article having a coating thereon, wherein the coating is formed from a coating formulation comprising a water-based hydrogel polymer, a first elastomeric material, and a second elastomeric material, wherein the coating formulation does not contain any added solvents, wherein the second elastomeric material is nitrile latex, and wherein the elastomeric article comprises a material that is the same as the first elastomeric material.

* * * * *